US008518887B2

(12) United States Patent
Noguera-Troise et al.

(10) Patent No.: US 8,518,887 B2
(45) Date of Patent: Aug. 27, 2013

(54) METHOD OF TREATING CANCER WITH DLL4 ANTAGONIST AND CHEMOTHERAPEUTIC AGENT

(75) Inventors: Irene Noguera-Troise, Staten Island, NY (US); Gavin Thurston, White Plains, NY (US); Alain Thibault, Bethesda, MD (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 228 days.

(21) Appl. No.: 12/823,680

(22) Filed: Jun. 25, 2010

(65) Prior Publication Data

US 2010/0330106 A1      Dec. 30, 2010

Related U.S. Application Data

(60) Provisional application No. 61/220,465, filed on Jun. 25, 2009, provisional application No. 61/301,881, filed on Feb. 5, 2010.

(51) Int. Cl.
| | |
|---|---|
| *A61K 38/00* | (2006.01) |
| *A61K 38/16* | (2006.01) |
| *A61K 33/24* | (2006.01) |
| *A61K 9/127* | (2006.01) |
| *A61P 35/00* | (2006.01) |
| *C07K 16/00* | (2006.01) |
| *C12P 21/08* | (2006.01) |

(52) U.S. Cl.
USPC ....... 514/19.2; 514/19.3; 514/19.4; 514/19.5; 514/21.2; 514/49; 530/387.1; 530/387.7; 530/387.9; 530/388.15; 530/389.7; 424/450; 424/649

(58) Field of Classification Search
None
See application file for complete search history.

(56) References Cited

U.S. PATENT DOCUMENTS

| | | |
|---|---|---|
| 7,488,806 B2 | 2/2009 | Papadopoulos et al. |
| 2006/0134121 A1 | 6/2006 | Thurston et al. |
| 2007/0213266 A1 | 9/2007 | Gill et al. |
| 2008/0014196 A1 | 1/2008 | Yan |
| 2008/0107648 A1 | 5/2008 | Noguera et al. |
| 2008/0175847 A1 | 7/2008 | Yan et al. |
| 2008/0181899 A1* | 7/2008 | Papadopoulos et al. ... 424/139.1 |
| 2008/0187532 A1 | 8/2008 | Gurney et al. |

FOREIGN PATENT DOCUMENTS

| | | |
|---|---|---|
| WO | 2007/028110 A2 | 3/2007 |
| WO | 2007/070671 A2 | 6/2007 |
| WO | 2007/143689 A2 | 12/2007 |
| WO | 2008/042236 A2 | 4/2008 |
| WO | 2008/076379 A2 | 6/2008 |

\* cited by examiner

*Primary Examiner* — Joanne Hama
*Assistant Examiner* — Ian Dang
(74) *Attorney, Agent, or Firm* — Alston & Bird LLP

(57) ABSTRACT

The invention provides methods for treating various types of cancer/tumor by administering the combination of Dll4 antagonists, in particular, Dll4 antibodies and fragments thereof that specifically bind human Dll4, and chemotherapeutic agents. Such combination therapies exhibit synergistic effects compared to the treatment with either agent alone. Thus, the methods of the invention are particularly beneficial for cancer patients who have low tolerance to the side effects caused by high dosages required for the treatment by either agent alone, by being able to reduce effective dosages. Pharmaceutical compositions and kits containing Dll4 antagonists and chemotherapeutic agents are also provided.

17 Claims, 5 Drawing Sheets

US 8,518,887 B2

METHOD OF TREATING CANCER WITH DLL4 ANTAGONIST AND CHEMOTHERAPEUTIC AGENT

CROSS-REFERENCE TO RELATED APPLICATIONS

This application claims the benefit under 35 U.S.C §119(e) of U.S. provisional application Nos. 61/220,465 filed Jun. 25, 2009 and 61/301,881 filed Feb. 5, 2010, both of which are herein specifically incorporated by reference in their entirety.

SEQUENCE LISTING

An ASCII compliant text file of the sequence listing is filed concurrently with the present specification pursuant to 37 CFR §1.52(e) and 37 CFR §1.821. The text file containing the sequence listing is named "Dll4-Chemo_SeqList", was created on May 27, 2010, and contains approximately 47.0 kilobytes. The contents of the text file are herein incorporated by reference.

BACKGROUND OF THE INVENTION

1. Field of the Invention

This invention relates to methods of treating cancers or tumors with a delta-like ligand 4 (Dll4) antagonist, in particular, human antibodies or fragments thereof that specifically bind human Dll4, in combination with one or more chemotherapeutic agents, and pharmaceutical compositions comprising a Dll4 antagonist and a chemotherapeutic agent.

2. Description of Related Art

Dll4 is a member of the Delta family of Notch ligands which exhibits highly selective expression by vascular endothelium (Shutter et al., 2000, *Genes Develop.* 14:1313-1318). Dll4 is a ligand for Notch receptors, including Notch 1 and Notch 4. Dll4 antagonists are useful for inhibiting tumor growth in various cancers. The nucleic acid and amino acid sequences for human Dll4 (hDll4) are shown in SEQ ID NOS:1 and 2, respectively. Antibodies specific for human Dll4 and cancer/tumor treatment using Dll4 antibodies are disclosed in international patent application publications WO 2007/143689, WO 2008/042236, and WO 2007/070671.

Chemotherapeutic agents are widely used for the treatment of cancer both alone and in combination with surgery and/or radiation therapy. Combination therapies using a Dll4 antagonist and chemotherapeutic agents are disclosed in US patent application publications US 2008/0014196 and US 2008/0107648.

BRIEF SUMMARY OF THE INVENTION

In a first aspect, the invention features a method of treating cancer in a subject in need thereof, comprising administering to the subject a Dll4 antagonist in combination with a chemotherapeutic agent, wherein the cancer is treated. The subject to be treated by the method of the invention may include any mammalian species, but preferably humans suffering from cancer.

The combination therapies of the present invention are particularly useful in Dll4-associated or Dll4-mediated condition or disease, which is affected directly or indirectly by modulation of Dll4 activity. More specifically, since Dll4 is now shown to be involved in blood vessel growth and development, inhibiting or reducing Dll4-mediated blood vessel growth or development or maturation using Dll4 antagonists, is an effective treatment for cancer/tumor that requires sufficient blood supply for its growth and survival. Furthermore, combining Dll4 antagonists with chemotherapeutic agents, including growth inhibitory agents and other cytotoxic agents, synergistically enhances their anti-cancer/anti-tumor effects. Cancers/tumors treatable by the methods of the present invention include, but not by way of limitation, various solid malignancies, including ovarian cancer, uterus cancer, breast cancer, lung cancer, liver cancer, colorectal cancer, bladder cancer, renal cancer, prostate cancer, pancreatic cancer, stomach cancer, bone cancer, skin cancer, including melanoma, malignant soft tissue sarcoma, including, but not limited to, Ewing's sarcoma, rhabdomyosarcoma, leiomyosarcoma, adipocytic sarcoma, synovial sarcoma, malignant fibrous histiocytoma, epithelioid hemangioendothelioma, angiosarcoma, fibrosarcoma, and unclassified sarcomas, leukemia, including myeloma, and the like.

In one embodiment, the Dll4 antagonist is a Dll4 antibody or fragment thereof ("Dll4 Ab") that specifically binds Dll4 with high affinity and blocks the binding of Dll4 to the Notch receptors and/or neutralizes Dll4 activities. The antibody may be polyclonal, monoclonal, chimeric, humanized, or a wholly human antibody. Preferably the antibody is a fully human monoclonal antibody or monoclonal antibody fragment. The antibody fragment may be a single chain antibody, an Fab, or an $(Fab')_2$.

In another embodiment, the Dll4 Ab binds an epitope within the N-terminal domain (S27-R172), or the DSL domain (V173-C217), or the N-terminal-DSL domain (S27-C217), of Dll4 (SEQ ID NO:2). The Dll4 Ab to be used in the methods of the invention is capable of binding human Dll4 with high affinity and its dissociation constant ($K_D$) is about 500 pM or less, including about 300 pM or less, and including about 200 pM or less, as measured by surface plasmon resonance. For example, the Dll4 Ab has a heavy chain variable region (HCVR) comprising three heavy chain CDRs (H-CDRs) and a light chain variable region (LCVR) comprising three light chain CDRs (L-CDRs), wherein the three heavy chain CDRs comprise CDR1, CDR2 and CDR3 of the amino acid sequence of SEQ ID NO:20 and the three light chain CDRs comprise CDR1, CDR2 and CDR3 of the amino acid sequence of SEQ ID NO:28. In another embodiment, the heavy chain CDR1, CDR2 and CDR3 of the Dll4 Ab comprise the amino acid sequences of SEQ ID NOS: 22, 24 and 26, respectively. In another embodiment, the light chain CDR1, CDR2 and CDR3 of Dll4 Ab comprise the amino acid sequences of SEQ ID NOS:30, 32 and 34, respectively. In yet another embodiment, the Dll4 Ab comprises heavy chain CDR1, CDR2 and CDR3 sequences comprising SEQ ID NO:22, 24 and 26, respectively, and light chain CDR1, CDR2 and CDR3 sequences comprising SEQ ID NO:30, 32 and 34, respectively. In yet another embodiment, the Dll4 Ab comprises a HCVR comprising the amino acid sequence of SEQ ID NO:20 or 116, or a LCVR comprising the amino acid sequence of SEQ ID NO:28 or 118. In yet another embodiment, the Dll4 Ab comprises a HCVR/LCVR combination of SEQ ID NO:20/28 (REGN281) or 116/118 (REGN421).

In another embodiment, the Dll4 Ab comprises a heavy chain CDR1/CDR2/CDR3 combination and a light chain CDR1/CDR2/CDR3 combination selected from: SEQ ID NO:6/8/10 and SEQ ID NO:14/16/18, respectively; SEQ ID NO:38/40/42 and SEQ ID NO:46/48/50, respectively; SEQ ID NO:54/56/58 and SEQ ID NO:62/64/66, respectively; SEQ ID NO:70/72/74 and SEQ ID NO:78/80/82, respectively; SEQ ID NO:86/88/90 and SEQ ID NO:94/96/98, respectively; and SEQ ID NO:102/104/106 and SEQ ID NO:110/112/114, respectively. In another embodiment, the Dll4 Ab comprises a HCVR comprising the amino acid sequence of SEQ ID NO:4, 36, 52, 68, 84, or 100, or a LCVR comprising the amino acid sequence of SEQ ID NO:12, 44, 60, 76, 92, or 108. In yet another embodiment, the Dll4 Ab comprises a HCVR/LCVR combination selected from: SEQ ID NO:4/12 (REGN279); SEQ ID NO:36/44 (REGN290); SEQ ID NO:52/60 (REGN306); SEQ ID NO:68/76 (REGN309); SEQ ID NO:84/92 (REGN310); and SEQ ID NO:100/108 (REGN289).

The nucleotide sequences encoding the amino acid sequences of SEQ ID NOS:4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116 and 118, are shown as SEQ ID NOS:3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115 and 117, respectively.

In one embodiment, the chemotherapeutic agent is an antimitotic agent, such as docetaxel, paclitaxel, and the like; a platinum-based chemotherapeutic compound, such as cisplatin, carboplatin, iproplatin, oxaliplatin, and the like; or other conventional cytotoxic agent, such as 5-fluorouracil (5-FU), capecitabine, irinotecan, leucovorin, gemcitabine; inhibitors of receptor tyrosine kinases and/or angiogenesis, such as ErbB inhibitors, RTK class III inhibitors, VEGFR inhibitors, and the like, and the Dll4 antagonist is a Dll4 antibody or fragment thereof as described above.

In a second aspect, the invention features a method of decreasing, reducing, or halting tumor growth in a subject in need thereof, comprising administering to the subject a Dll4 antagonist in combination with a chemotherapeutic agent, wherein tumor growth is decreased, reduced, or halted.

In a third aspect, the invention features a method of reducing the amount of a chemotherapeutic agent or a Dll4 antagonist necessary to achieve a desired therapeutic effect, compared to the administration of each agent alone, comprising administering the chemotherapeutic agent with a Dll4 antagonist. In one embodiment, the amount of a chemotherapeutic agent to achieve a desired therapeutic effect, such as, for example, halting or reducing tumor growth, is at least 10% less, at least 20% less, at least 30% less, at least 40% less, or at least 50% less, in the presence of co-administered Dll4 antagonist, or vice versa. In general, it is desirable that the amount of a chemotherapeutic agent or the Dll4 antagonist can be reduced by about 30% to about 50%. Thus, the methods of the invention are particularly beneficial for cancer patients who have low tolerance to the side effects caused by high dosages required for the treatment by either agent alone, by being able to reduce effective dosages.

In a fourth aspect, the invention features a pharmaceutical composition comprising a Dll4 antagonist, a chemotherapeutic agent, and a pharmaceutically acceptable carrier. In one embodiment, the Dll4 antagonist is a Dll4 Ab or fragment thereof that specifically binds to Dll4 with high affinity and neutralizes Dll4 activities, and the chemotherapeutic agent is any of those described herein.

In a fifth aspect, the invention features a kit comprising a container comprising the pharmaceutical composition of the present invention, and a package insert with an instruction for use. In one embodiment, a kit may comprise a container comprising therein an antibody or antigen-binding fragment thereof that specifically binds hDll4, one or more additional containers comprising therein at least one chemotherapeutic agent selected from any of those described herein, and a package insert with an instruction for use.

Other objects and advantages will become apparent from a review of the ensuing detailed description.

DETAILED DESCRIPTION

Figure 1:
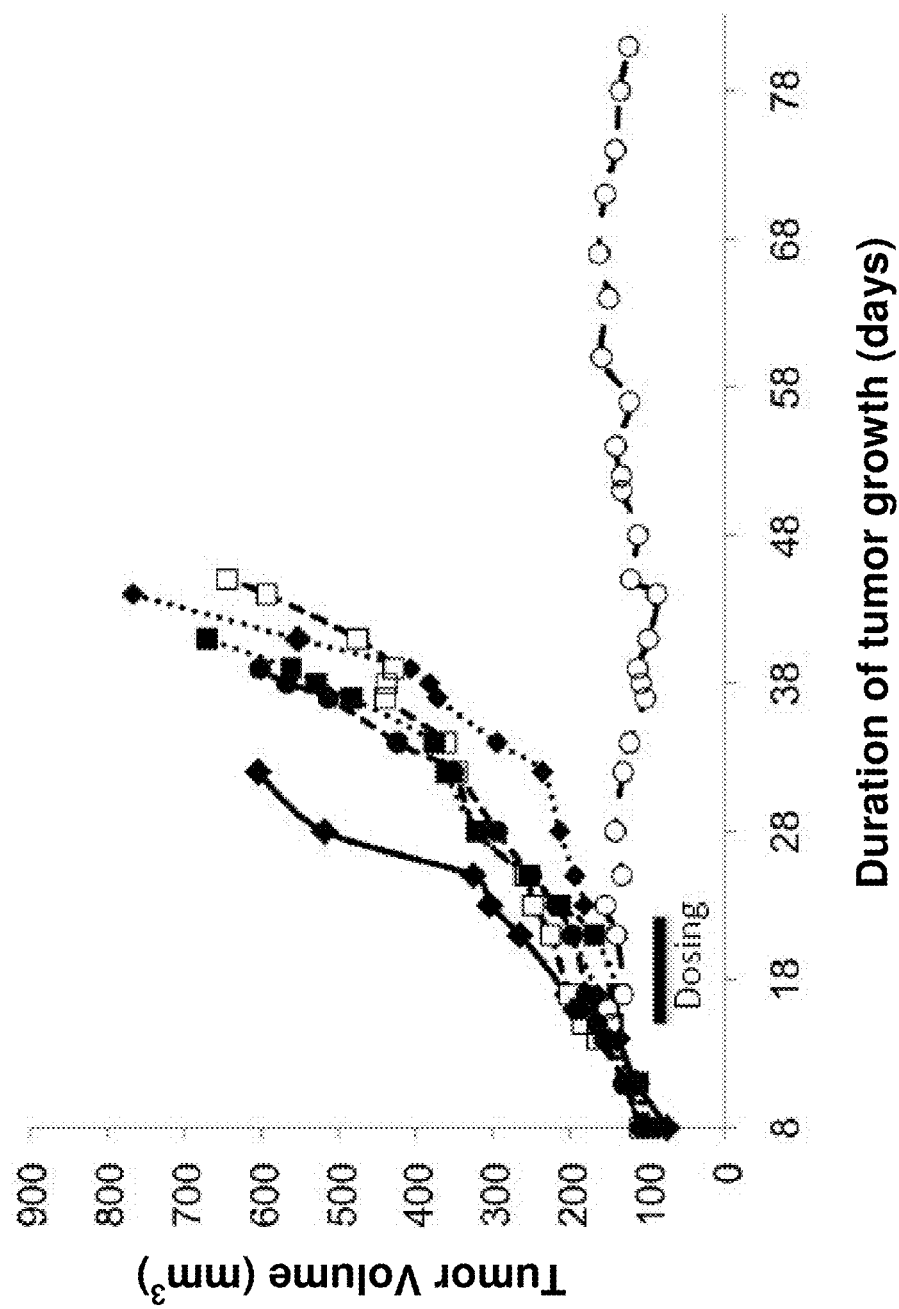
FIG. 1 shows the effects of Dll4 Ab in combination with cisplatin on the growth of human VMCub1 tumors (bladder carcinoma) implanted in Severe Combined Immunodeficiency (SCID) mice expressing humanized Dll4 protein (humanized Dll4 SCID mice) (Example 1). Human Fc control (♦ with solid line); REGN421 (Dll4 Ab) 2 mg/kg/injection (♦ with dashed line); cisplatin 0.5 mg/kg/injection (□); cisplatin 2 mg/kg/injection (■); REGN421 2 mg/kg/injection+cisplatin 0.5 mg/kg/injection (○); and REGN421 2 mg/kg/injection+cisplatin 2 mg/kg/injection (●).

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

DEFINITIONS

"Delta-like ligand 4", "Dll4", "hDll4" are used interchangeably to refer to the protein encoded by the nucleic acid sequence of SEQ ID NO:1 and the protein having the amino acid sequence of SEQ ID NO:2.

Dll4 antagonists include antibodies to Dll4 and fragments thereof capable of blocking the binding of Dll4 to a Notch receptor (such as Notch1 and Notch4), fusion proteins comprising the extracellular domain of Dll4 fused to a multimerizing component, or fragments thereof (see for example, US patent application publication nos. 2006/0134121 and 2008/0107648), and peptides and peptibodies (see for example, US patent application publication no. 2003/0229023).

Unless specifically indicated otherwise, the term "antibody," as used herein, shall be understood to encompass antibody molecules comprising two immunoglobulin heavy chains and two immunoglobulin light chains (La, "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The fully-human anti-Dll4 antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are back-mutated to the corresponding germline residue(s) or to a conservative amino acid substitution (natural or non-natural) of the corresponding germline residue(s) (such sequence changes are referred to herein as "germline back-mutations"). A person of ordinary skill in the art, starting with the heavy and light chain variable region sequences disclosed herein, can easily produce numerous antibodies and antigen-binding fragments which comprise one or more individual germline back-mutations or combinations thereof. In certain embodiments, all of the framework and/or CDR residues within the $V_H$ and/or $V_L$ domains are mutated back to the germline sequence. In other embodiments, only certain residues are mutated back to the germline sequence, e.g., only the mutated residues found within the first 8 amino acids of FR1 or within the last 8 amino acids of FR4, or only the mutated residues found within CDR1, CDR2 or CDR3. Furthermore, the antibodies of the present invention may contain any combination of two or more germline back-mutations within the framework and/or CDR regions, i.e., wherein certain individual residues are mutated back to the germline sequence while certain other residues that differ from the germline sequence are maintained. Once obtained, antibodies and antigen-binding fragments that contain one or more germline back-mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-Dll4 antibodies comprising variants of any of the HCVR, LCVR, and/or CDR amino acid sequences disclosed herein having one or more conservative substitutions. For example, the present invention includes anti-Dll4 antibodies having HCVR, LCVR, and/or CDR amino acid sequences with, e.g., 10 or fewer, 8 or fewer, 6 or fewer, 4 or fewer, 2 or 1, conservative amino acid substitution(s) relative to any of the HCVR, LCVR, and/or CDR amino acid sequences disclosed herein. In one embodiment, a HCVR comprises the amino acid sequence of SEQ ID NO:116 with 10 or fewer conservative amino acid substitutions therein. In another embodiment, a HCVR comprises the amino acid sequence of SEQ ID NO:116 with 8 or fewer conservative amino acid substitutions therein. In another embodiment, a HCVR comprises the amino acid sequence of SEQ ID NO:116 with 6 or fewer conservative amino acid substitutions therein. In another embodiment, a HCVR comprises the amino acid sequence of SEQ ID NO:116 with 4 or fewer conservative amino acid substitutions therein. In yet another embodiment, a HCVR comprises the amino acid sequence of SEQ ID NO:116 with 2 or 1 conservative amino acid substitution(s) therein. In one embodiment, a LCVR comprises the amino acid sequence of SEQ ID NO:118 with 10 or fewer conservative amino acid substitutions therein. In another embodiment, a LCVR comprises the amino acid sequence of SEQ ID NO:118 with 8 or fewer conservative amino acid substitutions therein. In another embodiment, a LCVR comprises the amino acid sequence of SEQ ID NO:118 with 6 or fewer conservative amino acid substitutions therein. In another embodiment, a LCVR comprises the amino acid sequence of SEQ ID NO:118 with 4 or fewer conservative amino acid substitutions therein. In yet another embodiment, a LCVR comprises the amino acid sequence of SEQ ID NO:118 with 2 or 1 conservative amino acid substitution(s) therein.

A "neutralizing" or "blocking" antibody, is intended to refer to an antibody whose binding to Dll4 results in inhibition of the biological activity of Dll4. This inhibition of the biological activity of Dll4 can be assessed by measuring one or more indicators of Dll4 biological activity. These indicators of Dll4 biological activity can be assessed by one or more of several standard in vitro or in vivo assays known in the art. For instance, the ability of an antibody to neutralize Dll4 activity is assessed by inhibition of Dll4 binding to a Notch receptor.

The term "specifically binds," or the like, means that an antibody or antigen-binding fragment thereof forms a complex with an antigen that is relatively stable under physiologic conditions. Specific binding can be characterized by an equilibrium dissociation constant of at least about $1\times10^{-6}$ M or less (e.g., a smaller $K_D$ denotes a tighter binding). Methods for determining whether two molecules specifically bind are well known in the art and include, for example, equilibrium dialysis, surface plasmon resonance, and the like. An isolated antibody that specifically binds hDll4 may, however, exhibit cross-reactivity to other antigens such as Dll4 molecules from other species. Moreover, multi-specific antibodies (e.g., bispecifics) that bind to hDll4 and one or more additional antigens are nonetheless considered antibodies that "specifically bind" hDll4, as used herein.

The term "$K_D$", as used herein, is intended to refer to the dissociation constant of a particular antibody-antigen interaction.

The term "high affinity" antibody refers to those antibodies that bind Dll4 with a $K_D$ of less than about 500 pM, less than about 400 pM, less than about 300 pM, or less than about 200 pM, as measured by surface plasmon resonance, e.g., BIACORE™ or solution-affinity ELISA, using, for example, monomeric Dll4; or a $K_D$ of less than about 100 pM, less than about 50 pM, or less than about 20 pM, as measured by surface plasmon resonance, using, dimeric Dll4.

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.).

The term "epitope" is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

Chemotherapeutic agents are chemical compounds useful in the treatment of cancer and include growth inhibitory agents or other cytotoxic agents. Examples of chemotherapeutic agents that can be used in the present methods include alkylating agents such as thiotepa and cyclophosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-FU; folic acid analogues such as denopterin, methotrexate, pteropterin, trimetrexate; purine analogues such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; members of taxoid or taxane family, such as paclitaxel (TAXOL®, Bristol-Myers Squibb Oncology, Princeton, N.J.), docetaxel (TAXOTERE®; Aventis Antony, France) and analogues thereof; chlorambucil; gemcitabine; 6-thioguanine; mercaptopurine; methotrexate; platinum analogues such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; inhibitors of receptor tyrosine kinases and/or angiogenesis, including sorafenib (NEXAVAR® by Bayer Pharmaceuticals Corp.), sunitinib (SUTENT® by Pfizer), pazopanib (VOTRIENT™ by GlaxoSmithKline), toceranib (PALLADIA™ by Pfizer), vandetanib (ZACTIMA™ by AstraZeneca), cediranib (RECENTIN® by AstraZeneca), regorafenib (BAY 73-4506 by Bayer), axitinib (AG013736 by Pfizer), lestaurtinib (CEP-701 by Cephalon), erlotinib (TARCEVA® by Genentech), gefitinib (IRESSA™ by AstraZeneca), BIBW 2992 (TOVOK™ by Boehringer Ingelheim), lapatinib (TYKERB® by GlaxoSmithKline), neratinib (HKI-272 by Wyeth/Pfizer), and the like, and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (FARESTON®); and anti-androgens such as flutamide, nilutamide, bicalutamide, leuprolide, and goserelin; and pharmaceutically acceptable salts, acids or derivatives of any of the above. Other conventional cytotoxic chemical compounds as those disclosed in Wiemann et al., 1985, in Medical Oncology (Calabresi et aL., eds.), Chapter 10, McMillan Publishing, are also applicable to the methods of the present invention.

The term "growth inhibitory agents" refers to a compound or composition which inhibits growth of a cell, especially a cancer cell either in vitro or in vivo. Examples of growth inhibitory agents include agents that block cell cycle progression (at a place other than S phase), such as agents that induce G1 arrest and M-phase arrest. Classical M-phase blockers include the vincas (vincristine and vinblastine), taxane family members, including, but not limited to, paclitaxel (TAXOL®), docetaxel (TAXOTERE®), and analogues thereof (e.g., XRP9881 and XRP6258; see Ojima et al., *Curr Opin Investig Drugs* 4:737, 2003), and topoisomerase inhibitors, such as irinotecan, topotecan, camptothecin, lamellarin D, doxorubicin, epirubicin, daunorubicin, etoposide, and bleomycin. Those agents that arrest G1 also spill over into S-phase arrest, for example, DNA alkylating agents, such as tamoxifen, prednisone, dacarbazine, mechlorethamine, cisplatin, methotrexate, 5-FU, and ara-C.

General Description

The present invention is based on the findings that co-administration of a Dll4 antagonist, for example, a Dll4 antibody or fragment thereof that specifically binds Dll4 and blocks Dll4 activities, with a chemotherapeutic agent, for example, cisplatin or docetaxel, results in greater inhibition of tumor growth than either single agent. For a description of fully human Dll4 Ab, including recombinant human Dll4 Ab, see international patent application publication no. WO 2008/076379.

Methods of Preparing Dll4 Ab

Methods for preparing antibodies are known to the art. See, for example, Kohler & Milstein (1975) Nature 256:495-497; Harlow & Lane (1988) Antibodies: a Laboratory Manual, Cold Spring Harbor Lab., Cold Spring Harbor, N.Y.). Antibodies that are isolated from organisms other than humans, such as mice, rats, rabbits, cows, can be made more human-like through chimerization or humanization.

"Humanized" or chimeric forms of non-human (e.g., murine) antibodies are immunoglobulins, immunoglobulin chains or fragments thereof (such as Fv, Fab, Fab', F(ab')$_2$ or other antigen-binding subsequences of antibodies) that contain minimal sequences required for antigen binding derived from non-human immunoglobulin. They have the same or similar binding specificity and affinity as a mouse or other nonhuman antibody that provides the starting material for construction of a chimeric or humanized antibody. Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1 and IgG4. A typical chimeric antibody is thus a hybrid protein consisting of the V or antigen-binding domain from a mouse antibody and the C or effector domain from a human antibody. Humanized antibodies have variable region framework residues substantially from a human antibody (termed an acceptor antibody) and complementarity determining regions (CDR regions) substantially from a mouse antibody, (referred to as the donor immunoglobulin). See, Queen et al., *Proc. Natl. Acad Sci. USA* 86:10029-10033 (1989) and international patent application publication no. WO 90/07861 and U.S. Pat. Nos. 5,693,762, 5,693,761, 5,585,089, 5,530,101 and 5,225,539. The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See international patent application publication no. WO 92/22653. Certain amino acids from the human variable region framework residues are selected for substitution based on their possible influence on CDR conformation and/ or binding to antigen. Investigation of such possible influences may be performed by modeling, examination of the characteristics of the amino acids at particular locations, or empirical observation of the effects of substitution or mutagenesis of particular amino acids. For example, when an amino acid differs between a murine variable region framework residue and a selected human variable region framework residue, the human framework amino acid should usually be substituted by the equivalent framework amino acid from the mouse antibody when it is reasonably expected that the amino acid: (1) noncovalently binds antigen directly; (2) is adjacent to a CDR region; (3) otherwise interacts with a CDR region (e.g., is within about 6 Å of a CDR region), or (4) participates in the $V_L$-$V_H$ interface. Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. Other candidates for substitution are acceptor human framework amino acids that are unusual for a human immunoglobulin at that position. The variable region frameworks of humanized immunoglobulins usually show at least 85% sequence identity to a human variable region framework sequence or consensus of such sequences.

Methods for generating human antibodies include, for example, VELOCIMMUNE™ (Regeneron Pharmaceuticals), XENOMOUSE™ technology (Abgenix), the "minilocus" approach, and phage display. The VELOCIMMUNE™ technology (U.S. Pat. No. 6,596,541) encompasses a method of generating a high specificity fully human antibody to a select antigen. This technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody. In one embodiment, the cell is a CHO cell.

The XENOMOUSE™ technology (Green et al., 1994, *Nature Genetics* 7:13-21) generates a mouse having both human variable and constant regions from both the heavy chain and kappa light chain loci. In an alternative approach, others have utilized a 'minilocus' approach in which an exogenous Ig locus is mimicked through inclusion of individual genes from the Ig locus (see, for example, U.S. Pat. No. 5,545,807). The DNA encoding the variable regions can be isolated with or without being operably linked to the DNA encoding the human heavy and light chain constant region.

Alternatively, phage display or related display technologies can be used to identify antibodies, antibody fragments, such as variable domains, and heteromeric Fab fragments that specifically bind to Dll4. (see, for example, US patent application publication no. 2003/0229023).

Screening and selection of preferred immunoglobulins (antibodies) can be conducted by a variety of methods known to the art. Initial screening for the presence of monoclonal antibodies specific to Dll4 may be conducted through the use of ELISA-based methods or phage display, for example. A secondary screen is preferably conducted to identify and select a desired monoclonal antibody. Secondary screening may be conducted with any suitable method known to the art. One preferred method, termed "Biosensor Modification-Assisted Profiling" ("BiaMAP") is described in U.S. patent application publication no. 2004/101920. BiaMAP allows rapid identification of hybridoma clones producing monoclonal antibodies with desired characteristics. More specifically, monoclonal antibodies are sorted into distinct epitope-related groups based on evaluation of antibody:antigen interactions. Alternatively, ELISA-based, bead-based, or BIACORE®-based competition assays can be used to identify binding pairs that bind different epitopes of Dll4 and thus are likely to cooperate to bind the ligand with high affinity.

Methods of Administration

The present invention provides methods of treatment comprising administering to a subject an effective amount of a pharmaceutical composition comprising a Dll4 antagonist, such as a Dll4 Ab, and a chemotherapeutic agent, such as anti-mitotic agents, for example, docetaxel, paclitaxel, and the like (taxanes); platinum-based chemotherapeutic compounds, such as cisplatin, carboplatin, iproplatin, oxaliplatin, and the like; pyrimidine analogue, such as 5-Fu, capecitabine (XELODA®, Roche), and the like; topoisomerase inhibitors, such as irinotecan, topotecan, camptothecin, lamellarin D, and the like; and/or adjuvants, such as leucovorin (folinic acid), and the like (for details, see the definition section above).

The Dll4 antagonist and the chemotherapeutic agent can be co-administered together or separately. Where separate dosage formulations are used, the Dll4 antagonist and the chemotherapeutic agent can be administered concurrently, or separately at staggered times, i.e., sequentially.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu and Wu, 1987, *J. Biol. Chem.* 262:4429 4432). Methods of introduction include but are not limited to intradermal, intramuscular, intraperitoneal, intravenous, subcutaneous, intranasal, intraocular, epidural, and oral routes. The composition may be administered by any route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g., daily, weekly, monthly, etc.) or in combination with other agents. Pulmonary administration can also be employed, for example, by use of an inhaler or nebulizer, and formulation with an aerosolizing agent.

With respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly).

In another embodiment, the active agent can be delivered in a vesicle, or a liposome (see Langer (1990) *Science* 249: 1527-1533). In yet another embodiment, the active agent can be delivered in a controlled release system. In one embodiment, a pump may be used (see Langer (1990) supra). In another embodiment, polymeric materials can be used (see Howard et aL (1989) *J. Neurosurg.* 71:105). In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, *Proc. Natl. Acad. Sci.* USA 88:1864-1868), etc. Alternatively, a nucleic acid can be introduced intracellularly and incorporated within host cell DNA for expression, by homologous recombination.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, said implant being of a porous, non-porous, or gelatinous material, including membranes, such as sialastic membranes, fibers, or commercial skin substitutes.

The amount of the active agent of the invention which will be effective in the treatment of cancer/tumor can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 0.2 to 30 mg of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

The dose may vary depending upon the age and the size (e.g., body weight or body surface area) of a subject to be administered, target disease, conditions, route of administration, and the like. For systemic administration of Dll4 antagonists, in particular, for Dll4 antibodies, typical dosage ranges for intravenous administration are at a daily dose of about 0.01 to about 100 mg/kg of body weight, about 0.1 to about 50 mg/kg, or about 0.2 to about 10 mg/kg. For subcutaneous administration, the antibodies can be administered at about 10 mg to about 500 mg, about 20 mg to about 400 mg, about 30 mg to about 300 mg, or about 50 mg to about 200 mg, at the antibody concentration of, at least, about 25 mg/ml, about 50 mg/ml, about 75 mg/ml, about 100 mg/ml, about 125 mg/ml, about 150 mg/ml, about 175 mg/ml, about 200 mg/ml, or about 250 mg/ml, at least, 1 to 5 times per day, 1 to 5 times per week, or 1 to 5 times per month. Alternatively, the antibodies can be initially administered via intravenous injection, followed by sequential subcutaneous administration.

In general, chemotherapeutic agents are used intravenously or orally at a dose range of between 50 mg/m$^2$ and 5000 mg/m$^2$ per week, but the dosage ranges vary depending on various factors, including the subject being treated, the subject's weight and age, the severity of the affliction, the manner of administration, the type of chemotherapeutic agent being used, the judgment of the prescribing physician, and the like. The therapy may be repeated intermittently while symptoms are detectable or even when they are not detectable. The duration of the treatment may also vary depending on the severity of the conditions treated as well as tolerance levels of subjects for possible adverse effects, if any, and may last as long as necessary or so long as the benefit outweighs any adverse effect.

The dosage of each agent may be further adjusted in the combination therapy, where the amount of each agent necessary to achieve a desired therapeutic effect is reduced (i.e., exhibiting a synergistic effect), compared to the administration of either agent alone (see Examples 1 and 2, infra).

Chemotherapeutic agents that can be used in the combination therapies of the invention also include those which are employed in well-known chemotherapeutic regimens. For example, FOLFOX is a chemotherapeutic regimen for treating colorectal cancer (CRC) and is a combination of 5-FU, folinic acid and oxaliplatin. FOLFIRI is another chemotherapeutic regimen for CRC and is a combination of 5-FU, folinic acid and irinotecan. XELOX is a second-line chemotherapeutic regimen for CRC and is a combination of capecitabine and oxaliplatin.

Further, the therapy with the combination of a chemotherapeutic agent and a Dll4 antagonist may be provided alone or in combination with additional drugs, such as other anti-angiogenic agents, e.g., VEGF antagonists, including anti-VEGF antibodies (e.g., AVASTIN® by Genentech), VEGF-binding fusion proteins (e.g., aflibercept by Regeneron Pharmaceuticals), and the like, and other therapeutic agents, such as analgesics, anti-inflammatory agents, including nonsteroidal anti-inflammatory drugs (NSAIDS), such as Cox-2 inhibitors, and the like, so as to ameliorate and/or reduce the symptoms accompanying the underlying cancer/tumor.

Metronomic Chemotherapies

Metronomic chemotherapy is emerging as an improved way of administering chemotherapy. Traditional chemotherapy has been administered in single doses or short courses of therapy as the highest dose possible without causing lifethreatening levels of toxicity, e.g., at the maximum tolerated dose (MTD). MTD therapy requires prolonged breaks of 2-3 weeks between successive cycles of therapy. Despite the number of such chemotherapeutics and large number of clinical trials undertaken to test them, progress has been modest in terms of curing or significantly prolonging the lives of patients with cancer (Kerbel et al., 2004, *Nature Reviews Cancer* 4:423-436).

Metronomic chemotherapy refers to the frequent, even daily, administration of chemotherapeutics at doses significantly below the MTD, with no prolonged drug-free breaks. In addition to reduced acute toxicity, the efficacy of metronomic chemotherapy may increase when administered in combination with specific anti-angiogenic drugs, such as inhibitors of VEGF (Kerbel et al., 2004, supra).

Accordingly, the present invention features a metronomic chemotherapy for treating cancer in a subject in need thereof, comprising administering to the subject a Dll4 antagonist in combination with a chemotherapeutic agent, wherein the cancer is treated. In a specific embodiment, the Dll4 antagonist and a chemotherapeutic agent may be administered together or sequentially for a relatively short period of time, for example, 1-12 weeks, followed by metronomic administration of the chemotherapeutic agent over a prolonged period of time, for example, 6-24 months.

Pharmaceutical Compositions

The present invention provides pharmaceutical compositions comprising a Dll4 antagonist, a chemotherapeutic agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

A composition useful in practicing the methods of the invention may be a liquid comprising an agent of the invention in solution, in suspension, or both. The term "solution/suspension" refers to a liquid composition where a first portion of the active agent is present in solution and a second portion of the active agent is present in particulate form, in suspension in a liquid matrix. The liquid composition may be aqueous and also includes a gel and an ointment forms.

An aqueous suspension or solution/suspension useful for practicing the methods of the invention may contain one or more polymers as suspending agents. Useful polymers include water-soluble polymers such as cross-linked carboxyl-containing polymers. An aqueous suspension or solution/suspension of the present invention is preferably viscous or muco-adhesive, or even more preferably, both viscous and mucoadhesive.

Kits

The invention further provides an article of manufacturing or kit, comprising a packaging material, container and a pharmaceutical agent contained within the container, wherein the pharmaceutical agent comprises at least one Dll4 antagonist, such as Dll4 antibody, and at least one chemotherapeutic agent, and wherein the packaging material comprises a label or package insert which indicates that the Dll4 antagonist and chemotherapeutic agent can be used for treating cancer or reducing or halting tumor growth. In one embodiment, the Dll4 antagonist and the chemotherapeutic agent may be contained in separate containers; thus, the invention provides a kit comprising a container comprising therein an antibody or antigen-binding fragment thereof that specifically binds hDll4, and one or more additional containers comprising therein at least one chemotherapeutic agent.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.), but some experimental errors and deviations should be accounted for. Unless indicated otherwise, parts are parts by weight, temperature is in degrees Centigrade, and pressure is at or near atmospheric. (Figure error bars=mean±SEM).

Example 1

Effect of Anti-hDll4 Antibody in Combination with Cisplatin

The effect of anti-Dll4 antibody (REGN421) in combination with cisplatin (platinol, cis-diamminedichloroplatinum) on tumor growth was evaluated on tumors implanted in Severe Combined Immunodeficiency (SCID) mice expressing a humanized Dll4 protein (humanized Dll4 SCID mice). The humanized Dll4 SCID mouse was made by replacing the entire extracellular domain of the mouse Dll4 gene with the corresponding extracellular region of the human Dll4 gene (7 kb) in embryonic stem (ES) cells. Homozygous hDll4 mice were generated and bred into SCID background.

Each mouse was implanted subcutaneously (sc) with $1\times10^6$ human VM-Cub1 tumor cells (bladder carcinoma cells) plus MATRIGEL™ (BD Biosciences, #354234). After the tumors were established in the mice (tumor size of 150-200 mm$^3$, approximately 14 days after implantation), tumors were measured, randomized and treated with hFc, REGN421, cisplatin, or combination of REGN421 and cisplatin. A total of 45 mice were divided into nine groups (n=5 per cohort). The first group was treated subcutaneously (sc) with hFc at 2 mg/kg; the second and third groups were treated sc with REGN421 at 0.5 and 2 mg/kg, respectively; the fourth and fifth groups were treated intraperitoneally (ip) with cisplatin at 0.5 and 2 mg/kg, respectively; the sixth group was treated sc with REGN421 at 0.5 mg/kg and ip with cisplatin at 0.5 mg/kg; the seventh group was treated sc with REGN421 at 0.5 mg/kg and ip with cisplatin at 2 mg/kg; the eighth group was treated sc with REGN421 at 2 mg/kg and ip with cisplatin at 0.5 mg/kg; and the ninth group was treated sc with REGN421 at 2 mg/kg and ip with cisplatin at 2 mg/kg. REGN421 was administered every 3-4 days starting on day 14 and mice received three doses total. Cisplatin was administered every 24 hours starting on day 14; mice received four doses total.

To assess the effects of REGN421 and cisplatin as single agents or in combination treatments, the changes in tumor size were recorded. Tumor growth was measured three days before the initial REGN421 treatment, on the day of each REGN421 treatment (days 14, 17 and 21) and thereafter every 3-4 days until tumors reached ~600 mm$^3$ in size. In vivo tumor size was calculated using the formula (length× width$^2$)/2 (FIG. 1 and Table 1).

TABLE 1

| TREATMENT (mg/kg/dose) | TGI (%) | TGD (days) | Euthanized (day) |
|---|---|---|---|
| hFc | — | — | 32 |
| REGN421 (0.5) | −13.7 | 0 | 32 |
| REGN421 (2) | 83.1 | 12 | 44 |
| Cisplatin (0.5) | 60.7 | 13 | 45 |
| Cisplatin (2) | 53.8 | 9 | 41 |
| REGN421 (0.5) + cisplatin (0.5) | 4.4 | 2 | 34 |
| REGN421 (0.5) + cisplatin (2) | −0.8 | 0 | 28 |
| REGN421 (2) + cisplatin (0.5) | 104.8 | 49 | >81 |
| REGN421 (2) + cisplatin (2) | 57.9 | 7 | 39 |

Tumor Growth Inhibition, TGI, was determined by calculating the difference in tumor size for treated (T) versus vehicle control (C) tumor at the day the control cohort was euthanized (i.e., at day 32); TGI=[1−($T_{final}$−$T_{initial}$)/($C_{final}$−$C_{initial}$)]×100.

Tumor growth delay, TGD, was assessed as the difference in days between treated (T) versus control (C) tumors when each cohort reached a specified tumor size. The predetermined tumor size for this experiment was 600 mm$^3$.

The results show that treatment with REGN421 alone caused a 54% reduction in tumor growth. Treatment with cisplatin alone resulted in reduced tumor growth (61% reduction for the dose of 0.5 mg/kg/injection; and 54% reduction for the dose of 2 mg/kg/injection). The combination treatments produced higher reductions in tumor growth than either single agent treatment (104% reduction for 0.5 mg/kg/injection cisplatin plus 2 mg/kg/injection REGN421; and 58% reduction for 2 mg/kg/injection cisplatin plus 2 mg/kg/injection REGN421).

These results showed that the treatment of tumors with a combination of Dll4 blocker together with cisplatin, at 2 mg/kg/injection of Dll4 blocker and 0.5 mg/kg/injection cisplatin, can result in greater inhibition of tumor growth than either single agent.

Example 2

Effect of Anti-hDll4 Antibody in Combination with Cisplatin

The effect of REGN421 in combination with cisplatin on tumor growth was evaluated on tumors implanted in humanized Dll4 SCID mice, as described above. Each mouse was implanted subcutaneously (sc) with $5\times10^6$ human A549 tumor cells (non-small cell lung cancer or "NSCLC"). After the tumors were established in the mice (tumor size of 100-150 mm$^3$, approximately 29 days after implantation), tumors were measured, randomized and treated with hFc, REGN421, cisplatin or combination of REGN421 and cisplatin. A total of 36 mice were divided into 6 groups (n=6 per cohort). The first group was treated sc with hFc at 2 mg/kg; the second group was treated sc with REGN421 at 2 mg/kg; the third and fourth groups were treated ip with cisplatin at 2.5 and 4.5 mg/kg, respectively; the fifth group was treated sc with REGN421 at 2 mg/kg and ip with cisplatin at 2.5 mg/kg; and the sixth group was treated sc with REGN421 at 2 mg/kg and ip with cisplatin at 4.5 mg/kg. REGN421 was administered every 3-4 days starting on day 29 and mice received three doses total. Cisplatin was administered every 24 hours starting on day 29 and mice received two doses total.

Figure 2:
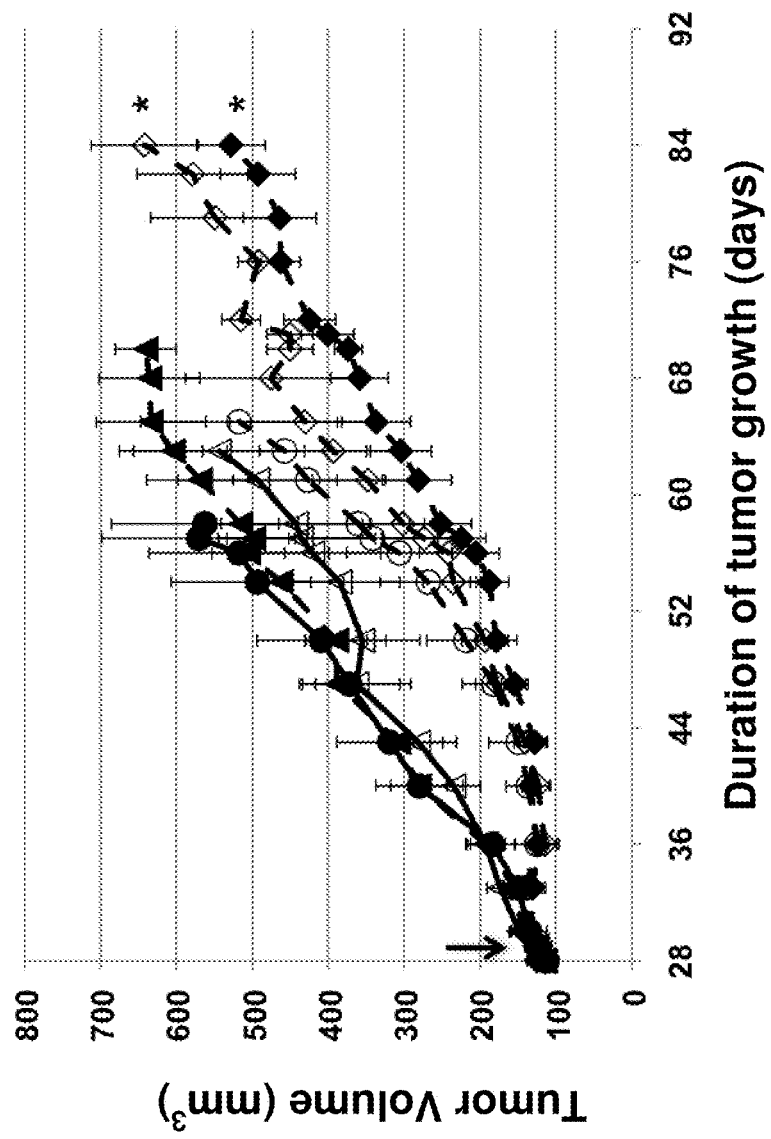
FIG. 2 shows the effects of Dll4 Ab in combination with cisplatin on the growth of human A549 tumors (non-small cell lung cancer) implanted in humanized Dll4 SCID mice (Example 2). Human Fc control (●); REGN421 6 mg/kg total dose (○); cisplatin 5 mg/kg total dose (Δ); cisplatin 9 mg/kg total dose (▲); REGN421 6 mg/kg+cisplatin 5 mg/kg total doses (◇); and REGN421 6 mg/kg+cisplatin 9 mg/kg total doses (♦).

To assess the effects of REGN421 and cisplatin as single agents or in combination we measured tumor size (volume), beginning three days before the initial REGN421 treatment, on the day of each agent treatment (days 29, 30, 33, 36) and thereafter every 3-4 days until tumors reached ~600 mm$^3$ in size. In vivo tumor size was calculated using the formula (length×width$^2$)/2. The effects on tumor growth are indicated in FIG. 2 and Table 2.

TABLE 2

| TREATMENT (mg/kg total dose) | TGI (%) at Day 57 | TGD (days) |
|---|---|---|
| hFc | — | — |
| REGN421 2 mg/kg (6) | 54 | 8 |
| Cisplatin 2.5 mg/kg (5) | 35 | 4 |
| Cisplatin 4.5 mg/kg (9) | 22 | 11 |
| REGN421 2 mg/kg (6) + Cisplatin 2.5 mg/kg (5) | 69 | 21 |
| REGN421 2 mg/kg (6) + Cisplatin 4.5 mg/kg (9) | 80 | 26 |

The results show that treatment with REGN421 alone caused a 54% reduction in tumor growth. Treatment with cisplatin alone resulted in reduced tumor growth (35% reduction for the dose of 2.5 mg/kg/injection; and 22% reduction for the dose of 4.5 mg/kg/injection). The combination treatments produced higher reductions in tumor growth than either single agent treatment (69% reduction for 2.5 mg/kg/injection of cisplatin plus 2 mg/kg/injection of REGN421; and 80% reduction for 4.5 mg/kg/injection of cisplatin plus 2 mg/kg/injection of REGN421). The combination treatments delayed tumor growth significantly (21 days for 2.5 mg/kg/injection of cisplatin plus 2 mg/kg/injection of REGN421; and 26 days for 4.5 mg/kg/injection of cisplatin plus 2 mg/kg/injection of REGN421), compared to control and either single agent ($p<0.01$).

These results show that treatment of tumors with a combination of Dll4 blocker together with cisplatin, at 2 mg/kg/injection of Dll4 blocker and 2.5-4.5 mg/kg/injection of cisplatin, can result in greater inhibition of tumor growth than either single agent.

Example 3

Effect of Anti-hDll4 Antibody in Combination with Docetaxel

The effect of anti-Dll4 antibody in combination with docetaxel (TAXOTERE®) on tumor growth was evaluated on tumors implanted in Severe Combined Immunodeficiency (SCID) mice. Each mouse was implanted subcutaneously (sc) with $1 \times 10^6$ rat C6 tumor cells (glioblastoma cells). After the tumors were established (tumor size of ~100-150 mm$^3$, approximately 13 days after implantation), the mice were treated with hFc, docetaxel, Dll4 antibody, or a combination of docetaxel plus Dll4 antibody. Since these mice expressed mouse Dll4, the Dll4 Ab used in this experiment was prepared in-house, based on the published sequence (WO 2007/143689), and designated as REGN 577. REGN 577 binds to human and mouse Dll4, but does not detectably binds human Dll1 and JAG1. A total of 30 tumor-bearing male mice were randomized into six groups (N=5). The first group was treated subcutaneously with hFc (at 25 mg/kg) and intravenously (iv) with vehicle; the second group was treated with REGN577 sc at 5 mg/kg; the third group was treated with docetaxel iv at 4.5 mg/kg; the fourth group was treated with docetaxel iv at 6 mg/kg; the fifth group was treated with docetaxel iv at 4.5 mg/kg plus REGN577 sc at 5 mg/kg; the sixth group was treated with docetaxel iv at 6 mg/kg plus REGN577 sc at 5 mg/kg. Docetaxel and/or Dll4 antibody were administered on the same day. Animals were treated 2 times per week and received a total of 3 doses. Starting from the day of initial treatment, body weight and tumors were measured twice a week until the mice were euthanized when tumors reached ~600 mm$^3$ in size. Tumor size was calculated using the formula, (length×width$^2$)/2.

The control tumors reached the size of ~600 mm$^3$ and were harvested on day 25. At Day 25, the results show that treatment with Dll4 antibody alone caused a modest reduction in tumor growth (by approximately 44%). Treatment with docetaxel alone resulted in reduced tumor growth (62% reduction for the dose of 4.5 mg/kg; and 70% reduction for the dose of 6 mg/kg). The combination treatments produced larger reductions in tumor growth (75% reduction for 4.5 mg/kg docetaxel plus Dll4 Ab; and 81% reduction for 6 mg/kg docetaxel plus Dll4 Ab) than control and either single agent treatment. TGI and TGD were determined (Table 3).

TABLE 3

| TREATMENT (mg/kg total dose) | TGI (%) at Day 25 | TGD (days) |
| --- | --- | --- |
| REGN577 5 mg/kg (15) | 44 | 3 |
| Docetaxel 4.5 mg/kg (13.5) | 62 | 6 |
| Docetaxel 6 mg/kg (18) | 70 | 7 |
| REGN577 5 mg/kg (15) + Docetaxel 4.5 mg/kg (13.5) | 75 | 10 |
| REGN577 5 mg/kg (15) + Docetaxel 6 mg/kg (18) | 81 | 13 |

These results show that treatment of tumors with a combination of Dll4 blocker together with various doses of docetaxel, can delay tumor growth almost twice as long and result in greater tumor growth inhibition than either single agent.

Example 4

Effect of Anti-hDll4 Antibody in Combination with Docetaxel

The effect of anti-Dll4 antibody in combination with docetaxel (TAXOTERE®, sanofi-aventis) on tumor growth was evaluated on tumors implanted in Severe Combined Immunodeficiency (SCID) mice. Each mouse was implanted 'pseudo-orthotopically' (subcutaneously into mammary gland #3) with $5 \times 10^6$ human MDA-MB-231 breast tumor cells with MATRIGEL™ (BD Biosciences lot #84540). After the tumors were established in the mice (tumor size of ~150-200 mm$^3$, approximately 45 days after implantation), mice were treated with hFc, docetaxel, Dll4 antibody, or a combination of docetaxel plus Dll4 antibody. A total of 25 tumor-bearing male mice were randomized into five groups (N=5 mice per group). The first group was treated subcutaneously with hFc (at 25 mg/kg) and intravenously (iv) with vehicle; the second group was treated with Dll4 antibody REGN577 sc at 5 mg/kg; the third group was treated with docetaxel iv at 4.5 mg/kg; the fourth group was treated with docetaxel iv at 6 mg/kg; the fifth group was treated with docetaxel iv at 6 mg/kg plus REGN577 sc at 5 mg/kg. Docetaxel and/or Dll4 antibody were administered on the same day. Animals were treated 2 times per week and received a total of 3 doses. Starting from the day of initial treatment, body weight and tumors were measured twice a week until the mice are euthanized. Mice were euthanized when tumors reached ~600 mm$^3$ in size. Tumor size was calculated using the formula (length× width$^2$)/2.

The control tumors reached ~600 mm$^3$ and were harvested on day 63. At Day 63, the results show that treatment with docetaxel alone produced modest reduction of tumor growth (37% reduction for the dose of 4.5 mg/kg; and 52% reduction for the dose of 6 mg/kg). Treatment with Dll4 antibody alone caused a significant reduction in tumor growth (approximately 85% reduction); meanwhile the combination treatment resulted in tumor regression (105% reduction for 6 mg/kg docetaxel plus Dll4 Ab). TGI and TGD were determined (Table 4).

TABLE 4

| TREATMENT (mg/kg total dose) | TGI (%) at Day 25 | TGD (days) |
| --- | --- | --- |
| REGN577 5 mg/kg (15) | 85 | 21 |
| Docetaxel 4.5 mg/kg (13.5) | 37 | 4 |
| Docetaxel 6 mg/kg (18) | 52 | 4 |
| REGN577 5 mg/kg (15) + Docetaxel 6 mg/kg (18) | 105 | 28 |

Docetaxel treatment alone resulted in minimal delay in tumor growth (4 days for the dose of 4.5 mg/kg; and 4 days for the dose of 6 mg/kg). Tumors treated with Dll4 antibody alone delayed tumor growth by 21 days. The combination treatments delayed tumor growth further, compared to control and either single agent treatment (28 days for 6 mg/kg docetaxel plus Dll4 Ab; p<0.5).

These results show that MDA-MB-231 tumors are modestly responsive to docetaxel treatment alone but are very sensitive to treatment with anti-Dll4 antibody. Combination of Dll4 blocker together with docetaxel can further delay tumor growth and slightly improve tumor growth inhibition (tumor regression) compared to either single agent.

Example 5

Effect of Anti-hDll4 Antibody in Combination with 5-FU

The effect of anti-Dll4 Ab (REGN421) in combination with 5-FU on tumor growth was evaluated on tumors implanted in humanized Dll4 SCID mice. Each mouse was implanted subcutaneously (sc) with 5×10$^6$ human HCT116 tumor cells (CRC). After the tumors were established in the mice (tumor size of ~150 mm$^3$, 22 days after implantation), tumors were measured and randomized. The mice were then treated with hFc, REGN421, 5-FU or combination of REGN421 and 5-FU. A total of 30 mice were divided into 6 groups (n=5 per cohort). The first group was treated sc with hFc at 2 mg/kg; the second group was treated sc with REGN421 at 2 mg/kg; the third and fourth groups were treated ip with 5-FU at 15 and 25 mg/kg, respectively; the fifth group was treated sc with REGN421 at 2 mg/kg and ip with 5-FU at 15 mg/kg; and the sixth group was treated sc with REGN421 at 2 mg/kg and ip with 5-FU at 25 mg/kg. REGN421 was administered every 3-4 days starting on day 22 and mice received three doses total. 5-FU was administered every 3-4 days starting on day 22 and mice received three doses total.

Figure 3:
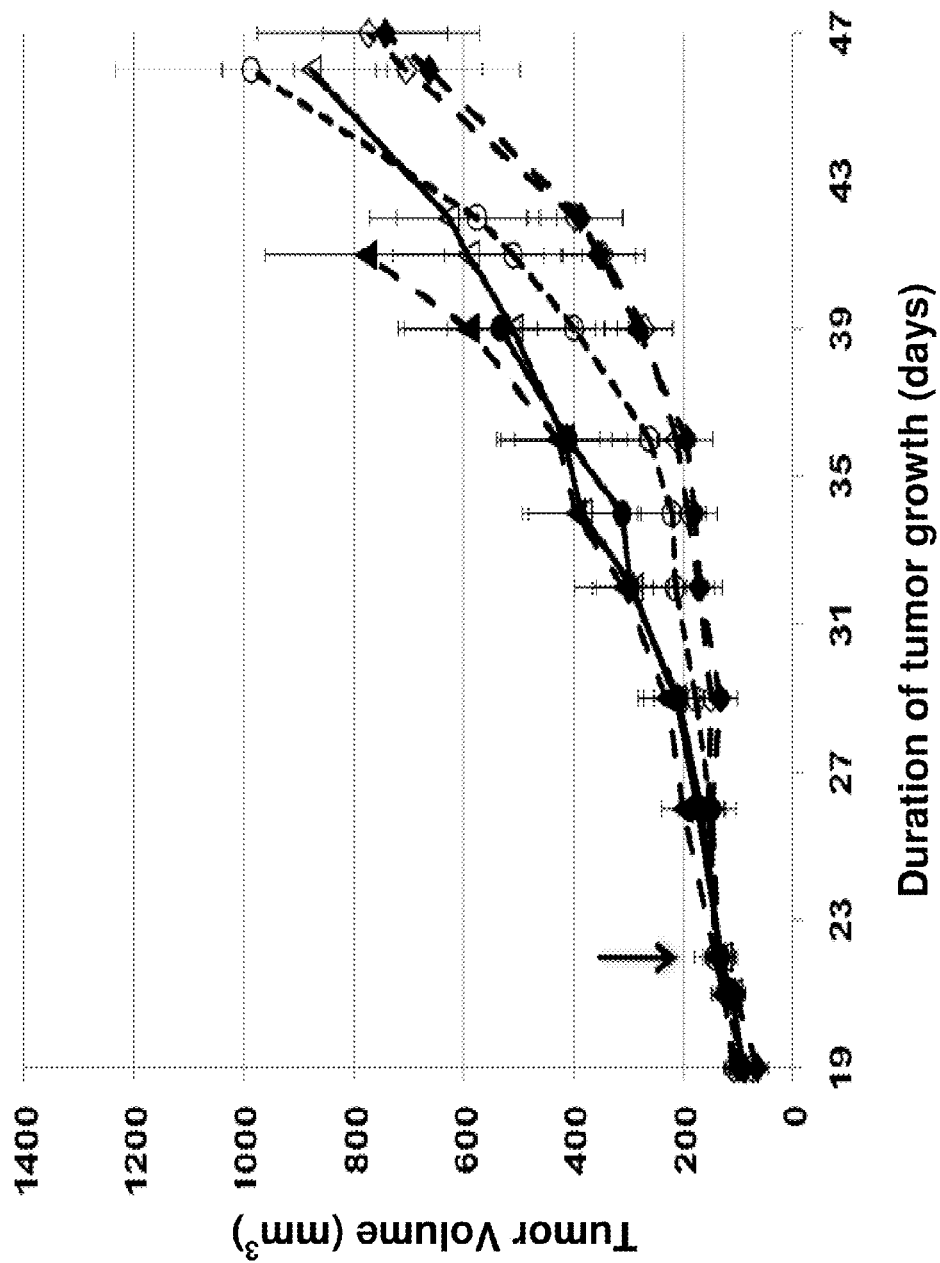
FIG. 3 shows the effects of Dll4 Ab in combination with 5-FU on the growth of human HCT116 (colorectal carcinoma) implanted in humanized Dll4 SCID mice (Example 5). Human Fc control (●); REGN421 6 mg/kg total dose (○); 5-FU 45 mg/kg total dose (Δ); 5-FU 75 mg/kg total dose (▲); REGN421 6 mg/kg+5-FU 45 mg/kg total doses (◇); and REGN421 6 mg/kg+5-FU 75 mg/kg total doses (♦).

To assess the effects of REGN421 and 5-FU as single agents or in combination, the changes in tumor size (volume) were measured, beginning three days before the initial REGN421 treatment, and then on the day of each agent treatment (days 22, 26, 29) and thereafter every 3-4 days until tumors reach ~600 mm$^3$ in size. In vivo tumor size is calculated using the formula (length×width$^2$)/2 (FIG. 3 and Table 5).

TABLE 5

| TREATMENT (mg/kg total dose) | TGI (%) at Day 39 | TGD (days) |
| --- | --- | --- |
| REGN421 2 mg/kg (6) | 36.3 | 6 |
| 5-FU 15 mg/kg (45) | 5.6 | 4 |
| 5-FU 25 mg/kg (75) | 0 | 2 |
| REGN421 2 mg/kg (6) + 5-FU 15 mg/kg 15 mg/kg (45) | 66.8 | 7 |
| REGN421 2 mg/kg (6) + 5-FU 25 mg/kg (75) | 63.3 | 7 |

5-FU treatment alone resulted in minimal delay in tumor growth (4 days for the total dose of 45 mg/kg; and 2 days for the total dose of 75 mg/kg). Tumors treated with Dll4 antibody alone delayed tumor growth by 6 days. The combination treatments delayed tumor growth further, compared to control (p<0.043).

Example 6

Effect of Anti-hDll4 Antibody in Combination with Irinotecan

The effect of anti-Dll4 Ab (REGN421) in combination with irinotecan (irinotecan hydrochloride) on tumor growth was evaluated on tumors implanted in humanized Dll4 SCID mice.

Each mouse was implanted subcutaneously (sc) with 5×10$^6$ human HCT116 tumor cells. After the tumors were established in the mice (tumor size of ~150 mm$^3$, 15 days after implantation), tumors were measured and randomized. The mice were then treated with hFc, REGN421, irinotecan or combination of REGN421 and irinotecan. A total of 30 mice were divided into 6 groups (n=5 per cohort). The first group was treated sc with hFc at 2 mg/kg; the second group was treated sc with REGN421 at 2 mg/kg; the third and fourth groups were treated ip with irinotecan at 7.5 and 25 mg/kg, respectively; the fifth group was treated sc with REGN421 at 2 mg/kg and ip with irinotecan at 7.5 mg/kg; and the sixth group was treated sc with REGN421 at 2 mg/kg and ip with irinotecan at 25 mg/kg. REGN421 was administered every 3-4 days starting on day 15 and mice received three doses total. Irinotecan was administered every 3-4 days starting on day 15 and mice received three doses total.

Figure 4:
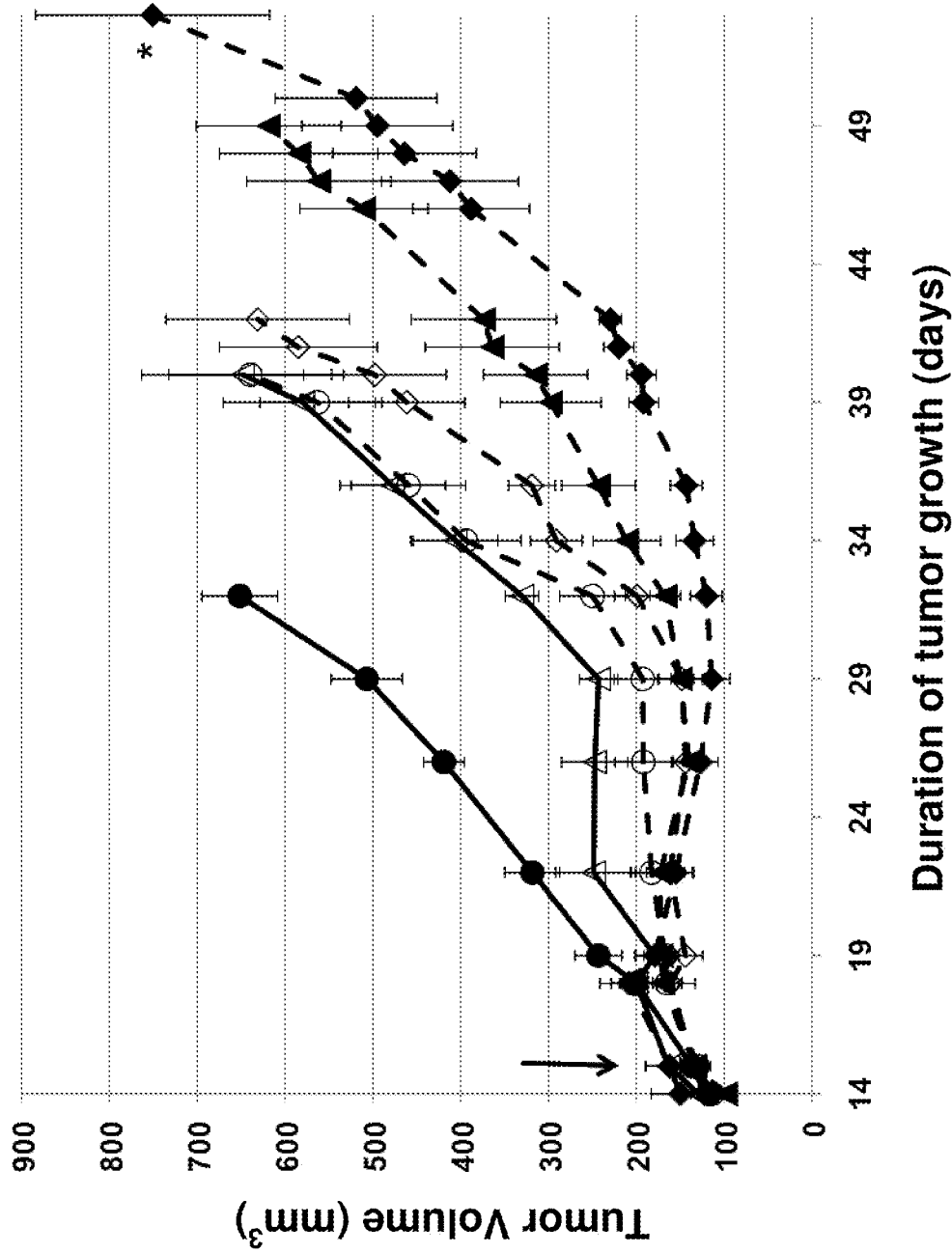
FIG. 4 shows the effects of Dll4 Ab in combination with Irinotecan on the growth of human HCT116 tumors implanted in humanized Dll4 SCID mice (Example 6). Human Fc control (●); REGN421 6 mg/kg total dose (○); irinotecan 22.5 mg/kg total dose (Δ); irinotecan 75 mg/kg total dose (▲); REGN421 6 mg/kg+irinotecan 22.5 mg/kg total doses (◇); and REGN421 6 mg/kg+irinotecan 75 mg/kg total doses (♦).

To assess the effects of REGN421 and irinotecan as single agents or in combination treatments, the changes in tumor size (volume) are measured, starting three days before the initial REGN421 treatment, and then on the day of each agent treatment (days 15, 19, 22) and thereafter every 3-4 days until tumors reach ~600 mm$^3$ in size. In vivo tumor size is calculated using the formula (length×width$^2$)/2. Results are shown in FIG. 4 and Table 6.

TABLE 6

| TREATMENT (mg/kg total dose) | TGI (%) at Day 39 | TGD (days) |
| --- | --- | --- |
| REGN421 2 mg/kg (6) | 81.3 | 9 |
| Irinotecan 7.5 mg/kg (22.5) | 71.2 | 8 |
| Irinotecan 25 mg/kg (75) | 100.5 | 16 |
| REGN421 2 mg/kg (6) + Irinotecan 7.5 mg/kg (22.5) | 91.5 | 10 |
| REGN421 2 mg/kg (6) + Irinotecan 25 mg/kg (75) | 119.6 | 19 |

Irinotecan treatment alone resulted in delay in tumor growth (8 days for the total dose of 22.5 mg/kg; and 16 days for the total dose of 75 mg/kg). Tumors treated with Dll4 antibody alone delayed tumor growth by 9 days. The combination treatments significantly improved anti-tumor efficacy and delayed tumor growth further, compared to either single agent treatment (19 days for 75 mg/kg irinotecan plus Dll4 Ab; p<0.0001).

Example 7

Effect of Anti-hDll4 Antibody on Hey1 Gene Expression in Colo205 Tumor

The effect of anti-hDll4 antibody on differential gene expression in tumors was studied in humanized Dll4 SCID mice implanted with human Colo205 colorectal tumor cells. Briefly, Male and female humanized Dll4 SCID mice were subcutaneously implanted with 2×10$^6$ Colo205 cells per mouse. When the tumors reached ~150 mm$^3$, mice (4 animals per group) were treated with a single dose of REGN421 at 0.5, 5 or 15 mg/kg, or of hFc control at 15 mg/kg. The tumors were excised at 5 hrs, 10 hrs, 24 hrs, 72 hrs and 7 days after the treatment and stored in RNA later stabilization reagent (Qiagen). Tumor RNA was purified using the RNEASY® Midi Kit (Qiagen). Tissue was homogenized in lysis buffer containing β-mercaptoethanol in a mixer mill, loaded onto the columns and unbound contaminants washed through. DNase I digestion was performed on the column and RNA was eluted in RNase-free water. Cyanine 3 (Cy3)-CTP was incorporated into amplified cRNA from 500 ng of total RNA using the QUICK AMP™ RNA Amplification Kit (Agilent Technologies). Cy3-labeled cRNA from each sample was then hybridized to a custom array covering both the mouse and human transcriptome. The hybridization and wash of the arrays were performed according to the manufacture's protocol and arrays were scanned on an Agilent Microarray scanner. The data were extracted from scanned array images using the Agilent Feature Extraction Software 9.5.

To identify genes differentially expressed between control and treatment groups, per-chip median centering is applied to the complete genomic profile of each sample. Gene expression values are then compared between two groups using a random variance model t-test (Simon, R. A. et al., 2007, "Analysis of Gene Expression Data Using BRB-Array Tools", *Cancer Inform* 3:11-7). Those genes with a mean difference greater than 1.5-fold and p-value<0.05 between the two groups are selected and ranked descending fold change. A global test is also performed in which the individual sample labels are permuted up to 1000 times and the gene selection process is repeated. This determines if the number of genes identified as differentially expressed between the two groups is more than would be expected by chance alone.

and 60. Plasma/serum levels of REGN421 in the samples are measured by ELISA with an upper limit of quantification of 2.5 µg/mL and a lower limit of quantification of 0.039 µg/mL in the undiluted serum sample. The study is ongoing with the intent to administer higher doses, defined in the protocol as 1, 2, 4, and 7 mg/kg/dose.

The currently available data showing plasma pharmacokinetic parameters following single 30-min. IV infusion of REGN421 at 0.25 mg/kg (7 patients) and 0.5 mg/kg (2 patients), are shown in Table 7. $C_{max}$: Maximum serum concentration of the drug; $T_{last}$: Time to the last quantifiable concentration of the drug; $C_{last}$: Last quantifiable concentration of the drug; $AUC_{last}$: Area under curve up to the last concentration of the drug; AUC: Total area under the curve (i.e., drug exposure); $t_{1/2Z}$: Terminal half life; $V_{ss}$: Volume of distribution at steady state; CL: Drug clearance rate. Values are: mean, (CV %), and [range] (a: median [range]).

TABLE 7

| Dose (mg/kg) | $C_{max}$ (µg/mL) | $T_{last}^{a}$ (h) | $C_{last}$ (µg/mL) | $AUC_{last}$ (µg * h/mL) | AUC (µg * h/mL) | $T_{1/2Z}$ (h) | $V_{ss}$ (L) | CL (L/h) |
|---|---|---|---|---|---|---|---|---|
| 0.25 (n = 7) | 6.27 (30.5) | 170 [72-240] | 0.51 (57.7) | 452 (56.7) | 489 (55.9) | 47.1 (33.5) | 2.85 (27.3) | 0.0473 (39.5) |
| 0.5 (n = 2) | 9.88 [9.25-10.5] | 203 [73-333] | 2.24 [0.976-3.51] | 759 [479-1040] | 963 [684-1240] | 92.3 [40.6-144] | 3.64 [2.65-4.63] | 0.0355 [0.0273-0.0436] |

Figure 5:
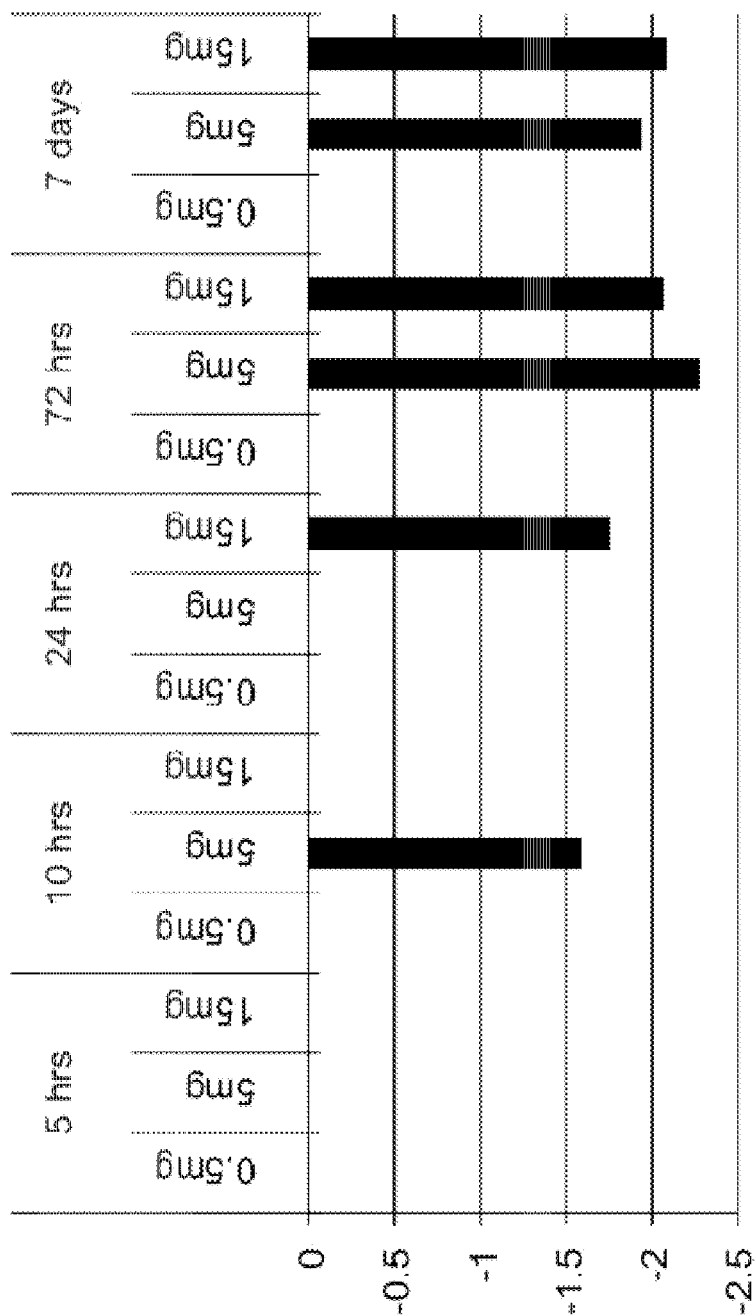
FIG. 5 shows the average (4 mice/group) fold changes of Hey1 gene expression in Colo205 human colorectal tumor cells implanted in humanized Dll4 SCID mice, with a single dose of REGN421 at 0.5, 5 or 15 mg/kg, compared to the hFc at 15 mg/kg, measured at 5, 10, 24 and 72 hours and 7 days post-dose.

Hey1 is a member of Hey family that has been identified as immediate downstream targets of Notch activation and it has been shown that inhibition of Dll4-Notch pathway signaling in tumors in vivo in mice studies results in the reduction of Hey-1 RNA levels (Noguera-Troise, I et al., 2006, *Nature* 444(7122):1032-7). As shown in FIG. 5, analysis of Hey1 mRNA levels in the current study using microarray revealed that Hey1 mRNA levels were decreased in the REGN421-treated mice compared to control hFc-treated mice starting at 10 hours post-treatment, but were most significantly decreased at 72 hours and 7 days post-treatment. No significant decrease was observed at 0.5 mg/kg, i.e., the lowest dose of REGN421. These results indicated that REGN421 effectively blocked the Notch signal pathway and that Hey1 could be a useful pharmacodynamic marker for inhibition of Notch signaling by a Dll4 antibody.

Example 8

Preliminary Pharmacokinetic Study in Phase I

REGN421 is currently being studied in a first-in-human trial. The primary objective of the study is to determine the recommended dose of REGN421 for future efficacy trials. The secondary objectives are to characterize the drug safety profile, its pharmacokinetics, immunogenicity, and pharmacodynamics, as well as preliminary evidence of efficacy. In this study, anti-hDll4 antibody REGN 421 is administered intravenously every 3 weeks to patients whose cancer has progressed on conventional therapy. The study design follows standard methodology for dose escalation and definition of dose-limiting toxicity. To date, 7 patients have been treated at 0.25 mg/kg/dose every three weeks, and 6 patients have been treated at 0.50 mg/kg/dose every three weeks. For the pharmacokinetic study, blood samples were taken at pre-dose, 0 hour, and post-dose 1, 2, 4 and 8 hours on Day 1, followed by Days 2, 3, 4, 8 and 15 of Cycle 1; and pre-dose, 0 hour on Day 1 of Cycles≧2, and post-treatment follow-up on Days 15, 30

The pharmacodynamic effect of REGN421 on the Dll4-notch signaling pathway has been analyzed using microarray technology on the patient serum samples collected prior to as well as 24 hours following REGN421 administration. The results are shown in Table 8.

TABLE 8

| Patient | Dose (mg/kg) | Hey-1 transcript Post-treatment vs. Pre-treatment ratio |
|---|---|---|
| 1 | 0.25 | 0.52 |
| 2 | 0.25 | 0.85 |
| 3 | 0.25 | 0.77 |
| 4 | 0.25 | 0.51 |
| 5 | 0.25 | 0.61 |
| 6 | 0.25 | 0.55 |
| 7 | 0.25 | 0.75 |
| 8 | 0.5 | 0.68 |
| 9 | 0.5 | 0.82 |

As shown in Table 8, the expression of the Hey-1 gene upon REGN421 administration was reduced compared to pre-treatment samples, in all samples. As observed in the xenograft tumor model in humanized Dll4 SCID mice (see Example 7 above), the findings suggest that REGN421 is indeed inhibiting the biological activity of Dll4 in humans.

Example 9

Dll4 Ab in Combination with Gemcitabine to Phase I Patients

The study will be conducted in adult patients with advanced or metastatic cancer that is refractory to standard therapy or have no approved treatment options. Patients who are diagnosed The study will be conducted in adult patients with advanced or metastatic cancer that is refractory to standard therapy or have no approved treatment options. Patients who are diagnosed to have advanced solid malignancies according to pathological, physical and radiological examination, with an ECOG (Eastern Cooperative Oncology Group) performance status score of 0-2 (0-5 scale) and adequate renal, hepatic and hematological laboratory parameters are eligible for participation in the study. Patients are allowed to receive concurrent supportive care, such as blood transfusions and analgesics, during the study. Patients may have received prior chemotherapy or biologic therapy for metastatic disease. Patients are assigned in sequential dosing cohorts in a 3+3 design. Three patients will be enrolled at one dose level and, if no dose limiting toxicities (DLT) occur, dose escalation to the next dose level will transpire. If 1 of the first 3 patients experiences a DLT, then 3 additional patients may be enrolled at that dose level. If 2 of the first 3 patients experience a DLT, then that dose level will be considered to have excessive toxicity, and 3 additional patients will be enrolled at the previous dose level. Patients will receive Day 1: anti-Dll4 antibody (e.g., REGN421 or REGN281) at 0.25 to 10 mg/kg IV over 30 minutes plus gemcitabine 1250 mg/m$^2$ IV infusion over 30 minutes and Day 8: gemcitabine 1250 mg/m$^2$ IV infusion over 30 minutes. The combination regimen is repeated every 3 weeks until cancer progression or intolerable toxicity develops.

The primary end point is to assess the safety, tolerability, and dose-limiting toxicities of the anti-Dll4 antibody in combination with gemcitabine and to identify the maximum tolerated dose (MTD) of the anti-Dll4 antibody in combination with gemcitabine in patients with advanced solid malignancies. The secondary end points include a description of anti-tumor activity according to RECIST criteria (by Eisenhauer et al., 2009, *Eur J Cancer* 4 5:228-247), assessment of the pharmacokinetic (PK) profile of the anti-Dll4 antibody when given in combination with gemcitabine and determination of immunogenicity to the anti-Dll4 antibody. Disease remission is evaluated using physical examination, radiological methods (X-Ray, Computed Tomography, or Magnetic Resonance Imaging). Adverse events are assessed using the National Cancer Institute Common Terminology Criteria for Adverse Events (CTCAE v 4.0, available under Cancer Therapy Evaluation Program or CTEP at the National Cancer Institute web site). Serum samples are taken from the patients to measure the concentrations of the anti-Dll4 antibody as well as the presence of possible antibodies against the anti-Dll4 antibody.

Example 10

Administration of Dll4 Ab and FOLFOX to CRC Patients

Briefly, adult patients who are diagnosed to have locally advanced or metastatic colorectal cancer according to pathological, physical and radiological examination, with an ECOG (Eastern Cooperative Oncology Group) performance status score of 0-2 (0-5 scale) and adequate renal, hepatic and hematological laboratory parameters are eligible for participation in the study. Patients are allowed to receive concurrent supportive care, such as blood transfusions and analgesics, during the study. Patients may not have received prior chemotherapy (or anti-angiogenic, or anti EGFR therapy) for metastatic disease; prior such therapy for the adjuvant treatment of their disease is allowed, and must have been completed at least 12 months prior to enrollment on this study. The patients are randomly assigned in a 1:1 ratio to receive intravenous FOLFOX chemotherapy (Day 1: Oxaliplatin 85 mg/m$^2$ IV infusion and leucovorin (folinic acid) 200 mg/m$^2$ IV infusion, followed by 5-FU 400 mg/m$^2$ IV bolus given over 2-4 minutes, followed by 5-FU 600 mg/m$^2$ IV as a 22-hour continuous infusion. Day 2: Leucovorin 200 mg/m$^2$ IV infusion, followed by 5-FU 400 mg/m$^2$ IV bolus given over 2-4 minutes, followed by 5-FU 600 mg/m$^2$ IV infusion as a 22-hour continuous infusion) with bevacizumab (AVASTIN®: Humanized monoclonal Ab against vascular endothelial growth factor (VEGF), Genentech) (Day 1: 10 mg/kg IV) every 2 weeks, or an anti-Dll4 antibody (REGN421) at 0.25 to 10 mg/kg IV on day 1, in combination with the previously mentioned treatment. The treatment is repeated every 2 weeks until cancer progression or intolerable toxicity develops.

The primary end point is the proportion of patients who have achieved at least a partial remission (a 30% or more decrease in the sum of diameters of identified cancer lesions, according to RECIST criteria (by Eisenhauer et al., 2009, supra) and the secondary end points include time to tumor progression, and overall survival. Disease remission is evaluated using physical examination, radiological methods (X-Ray, Computed Tomography, or Magnetic Resonance Imaging), and the Carcino-Embryonic Antigen (CEA) level measured in serum. Other clinical parameters, such as adverse events are also assessed, using the National Cancer Institute Common Terminology Criteria for Adverse Events (CTCAE v 4.0, supra). The patients' serum samples are taken to measure the serum concentrations of the anti Dll4 antibody as well as the presence of possible antibodies against the anti-Dll4 antibody.

Example 11

Phase II of Dll4 Ab in Combination with Docetaxel

The study will be conducted in adult patients with advanced inoperable or metastatic breast cancer. They may have failed prior adjuvant therapy. Patients who are diagnosed to have breast cancer according to pathological, physical and radiological examination, with an ECOG (Eastern Cooperative Oncology Group) performance status score of 0-2 (in 0-5 scale) and adequate renal, hepatic and hematological laboratory parameters are eligible for participation in the study. Patients are allowed to receive concurrent supportive care, such as blood transfusions and analgesics, during the study. Patients may not have received prior chemotherapy or biologic therapy for metastatic disease. A sequential cohort of up to 100 patients will be treated after successfully passing screening procedures to determine patient eligibility. Patients will receive Day 1: anti-Dll4 antibody (REGN421) at 0.25 to 10 mg/kg IV over 30 minutes plus docetaxel 75 mg/m$^2$ IV infusion over 30 minutes. The combination regimen is repeated every 3 weeks until cancer progression or intolerable toxicity develops.

The primary end point is to assess the efficacy of the treatment based on tumor response rate according to RECIST criteria (by Eisenhauer et al., 2009, *Eur J Cancer* 4 5:228-247), and time to disease progression. Secondary endpoints will include a description of the safety and of the pharmacokinetic (PK) profile of the anti-Dll4 antibody when given in combination with docetaxel as well as determination of immunogenicity to the anti-Dll4 antibody. Disease remission is evaluated using physical examination, radiological methods (X-Ray, Computed Tomography, or Magnetic Resonance Imaging). Adverse events are assessed using the National Cancer Institute Common Terminology Criteria for Adverse Events (CTCAE v 4.0, available under Cancer Therapy Evaluation Program or CTEP at the National Cancer Institute web site). Serum samples are taken from the patients to measure the concentrations of the anti-Dll4 antibody as well as the presence of possible antibodies against the anti-Dll4 antibody.

Example 12

A Phase II Study of Dll4 Ab with Cisplatin/Gemcitabine

The study will be conducted in adult patients with advanced inoperable or metastatic bladder cancer. Patients who are diagnosed to have invasive bladder cancer according to pathological, physical and radiological examination, with an ECOG (Eastern Cooperative Oncology Group) performance status score of 0-2 (in 0-5 scale) and adequate renal, hepatic and hematological laboratory parameters are eligible for participation in the study. Patients are allowed to receive concurrent supportive care, such as blood transfusions and analgesics, during the study. Patients may not have received prior chemotherapy or biologic therapy for metastatic disease. A sequential cohort of up to 100 patients will be treated after successfully passing screening procedures to determine patient eligibility. Patients will receive anti-Dll4 antibody (REGN421) at 0.25 to 10 mg/kg IV over 30 minutes on day 1 plus gemcitabine 1,000 mg/m$^2$ over 30 to 60 minutes on days 1, 8, and 15, plus cisplatin 70 mg/m$^2$ on day 2. The combination regimen is repeated every 4 weeks until cancer progression or intolerable toxicity develops.

The primary end point is to assess the efficacy of the treatment based on tumor response rate according to RECIST criteria (by Eisenhauer et al., 2009, *Eur J Cancer* 4 5:228-247), and time to disease progression. Secondary endpoints will include safety profile and a description of the pharmacokinetic (PK) profile of the anti-Dll4 antibody when given in combination with docetaxel and determination of immunogenicity to the anti-Dll4 antibody. Disease remission is evaluated using physical examination, radiological methods (X-Ray, Computed Tomography, or Magnetic Resonance Imaging). Adverse events are assessed using the National Cancer Institute Common Terminology Criteria for Adverse Events (CTCAE v 4.0, available under Cancer Therapy Evaluation Program or CTEP at the National Cancer Institute web site). Serum samples are taken from the patients to measure the concentrations of the anti-Dll4 antibody as well as the presence of possible antibodies against the anti-Dll4 antibody.

The invention claimed is:

1. A method of treating cancer or reducing or halting tumor growth in a subject, comprising administering to the subject an antibody or fragment thereof that specifically binds to human delta-like 4 (hDll4) and a chemotherapeutic agent such that cancer is treated, wherein said antibody or fragment thereof comprises a heavy chain variable region (HCVR) comprising heavy chain CDR1, CDR2 and CDR3 sequences of SEQ ID NO:22, 24 and 26, respectively, and a light chain variable region (LCVR) comprising light chain CDR1, CDR2 and CDR3 sequences of SEQ ID NO:30, 32 and 34, respectively.

2. The method of claim 1, wherein said antibody binds an epitope in the N-terminal domain or DSL domain, or both, of human Dll4.

3. The method of claim 1, wherein said antibody comprises a HCVR sequence of SEQ ID NO:20 or SEQ ID NO:116.

4. The method of claim 1, wherein said antibody comprises a LCVR sequence of SEQ ID NO: 28 or SEQ ID NO:118.

5. The method of claim 1, wherein said antibody comprises a HCVR/LCVR combination of SEQ ID NO:20/28 or 116/118.

6. The method of claim 1, wherein the chemotherapeutic agent is at least one selected from the group consisting of an anti-mitotic agent, platinum-based chemotherapeutic agent, pyrimidine analogue, topoisomerase inhibitor, receptor tyrosine kinase inhibitor, and adjuvant.

7. The method of claim 6, wherein the anti-mitotic agent is docetaxel or paclitaxel, or a pharmaceutically acceptable analogue or salt thereof.

8. The method of claim 6, wherein the platinum-based chemotherapeutic agent is cisplatin, carboplatin, iproplatin, or oxaliplatin, or a pharmaceutically acceptable salt thereof.

9. The method of claim 6, wherein the receptor tyrosine kinase inhibitor is sorafenib, sunitinib, or pazopanib, or a pharmaceutically acceptable salt thereof.

10. The method of claim 6, wherein the pyrimidine analogue is gemcitabine, 5-FU, or capecitabine, or a pharmaceutically acceptable salt thereof.

11. The method of claim 6, wherein the topoisomerase inhibitor is irinotecan, topotecan, camptothecin, or lamellarin D, or a pharmaceutically acceptable salt thereof.

12. The method of claim 6, wherein the adjuvant is folinic acid, or a pharmaceutically acceptable salt thereof.

13. The method of claim 1, wherein the chemotherapeutic agent is a combination of 5-FU, folinic acid and oxaliplatin; 5-FU, folinic acid and irinotecan; capecitabine and oxaliplatin; or cisplatin and gemcitabine.

14. The method of claim 1, wherein the cancer treated is selected from the group consisting of ovarian cancer, uterus cancer, breast cancer, lung cancer, liver cancer, colorectal cancer, bladder cancer, renal cancer, prostate cancer, pancreatic cancer, stomach cancer, bone cancer, skin cancer, leukemia, and malignant soft tissue sarcoma.

15. The method of claim 1, wherein the antibody or antigen-binding fragment and the chemotherapeutic agent are administered concurrently.

16. The method of claim 1, wherein the antibody or antigen-binding fragment and the chemotherapeutic agent are administered sequentially.

17. The method of claim 1, wherein the subject is a human subject.

* * * * *

SEQUENCE LISTING

```
<160> NUMBER OF SEQ ID NOS: 118

<210> SEQ ID NO 1
<211> LENGTH: 2058
<212> TYPE: DNA
<213> ORGANISM: Homo sapiens

<400> SEQUENCE: 1
atggcggcag cgtcccggag cgcctctggc tgggcgctac tgctgctggt ggcactttgg      60
cagcagcgcg cggccggctc cggcgtcttc cagctgcagc tgcaggagtt catcaacgag     120
cgcggcgtac tggccagtgg gcggccttgc gagcccggct gccggacttt cttccgcgtc     180
tgccttaagc acttccaggc ggtcgtctcg cccggaccct gcaccttcgg gaccgtctcc     240
acgccggtat tgggcaccaa ctccttcgct gtccgggacg acagtagcgg cggggggcgc     300
aaccctctcc aactgccctt caatttcacc tggccgggta ccttctcgct catcatcgaa     360
gcttggcacg cgccaggaga cgacctgcgg ccagaggcct tgccaccaga tgcactcatc     420
agcaagatcg ccatccaggg ctccctagct gtgggtcaga actggttatt ggatgagcaa     480
accagcaccc tcacaaggct gcgctactct taccgggtca tctgcagtga caactactat     540
ggagacaact gctcccgcct gtgcaagaag cgcaatgacc acttcggcca ctatgtgtgc     600
cagccagatg gcaacttgtc ctgcctgccc ggttggactg gggaatattg ccaacagcct     660
atctgtcttt cgggctgtca tgaacagaat ggctactgca gcaagccagc agagtgcctc     720
tgccgcccag gctggcaggg ccggctgtgt aacgaatgca tcccccacaa tggctgtcgc     780
cacggcacct gcagcactcc ctggcaatgt acttgtgatg agggctgggg aggcctgttt     840
tgtgaccaag atctcaacta ctgcacccac cactccccat gcaagaatgg ggcaacgtgc     900
tccaacagtg ggcagcgaag ctacacctgc acctgtcgcc caggctacac tggtgtggac     960
tgtgagctga gctcagcga gtgtgacagc aaccctgtc gcaatggagg cagctgtaag    1020
gaccaggagg atggctacca ctgcctgtgt cctccgggct actatggcct gcattgtgaa    1080
```

```
cacagcacct tgagctgcgc cgactccccc tgcttcaatg ggggctcctg ccgggagcgc    1140 aaccagggggg ccaactatgc ttgtgaatgt ccccccaact tcaccggctc caactgcgag    1200
aagaaagtgg acaggtgcac cagcaacccc tgtgccaacg ggggacagtg cctgaaccga    1260
ggtccaagcc gcatgtgccg ctgccgtcct ggattcacgg gcacctactg tgaactccac    1320
gtcagcgact gtgcccgtaa cccttgcgcc acggtggca cttgccatga cctggagaat    1380
gggctcatgt gcacctgccc tgccggcttc tctggccgac gctgtgaggt gcggacatcc    1440
atcgatgcct gtgcctcgag tccctgcttc aacagggcca cctgctacac cgacctctcc    1500
acagacacct ttgtgtgcaa ctgcccttat ggctttgtgg gcagccgctg cgagttcccc    1560
gtgggcttgc cgcccagctt ccctgggtg gccgtctcgc tgggtgtggg gctggcagtg    1620
ctgctggtac tgctgggcat ggtggcagtg gctgtgcggc agctgcggct tcgacggccg    1680
gacgacggca gcagggaagc catgaacaac ttgtcggact tccagaagga caacctgatt    1740
cctgccgccc agcttaaaaa cacaaaccag aagaaggagc tggaagtgga ctgtggcctg    1800
gacaagtcca actgtggcaa acagcaaaac cacacattgg actataatct ggccccaggg    1860
cccctggggc gggggaccat gccaggaaag tttccccaca gtgacaagag cttaggagag    1920
aaggcgccac tgcggttaca cagtgaaaag ccagagtgtc ggatatcagc gatatgctcc    1980
cccagggact ccatgtacca gtctgtgtgt ttgatatcag aggagaggaa tgaatgtgtc    2040
attgccacgg aggtataa                                                  2058
```

<210> SEQ ID NO 2
<211> LENGTH: 685
<212> TYPE: PRT
<213> ORGANISM: Homo sapiens

<400> SEQUENCE: 2

```
Met Ala Ala Ala Ser Arg Ser Ala Ser Gly Trp Ala Leu Leu Leu Leu
 1               5                  10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205
```

```
Leu Pro Gly Trp Thr Gly Glu Tyr Cys Gln Gln Pro Ile Cys Leu Ser
    210                 215                 220
Gly Cys His Glu Gln Asn Gly Tyr Cys Ser Lys Pro Ala Glu Cys Leu
225                 230                 235                 240
Cys Arg Pro Gly Trp Gln Gly Arg Leu Cys Asn Glu Cys Ile Pro His
                245                 250                 255
Asn Gly Cys Arg His Gly Thr Cys Ser Thr Pro Trp Gln Cys Thr Cys
            260                 265                 270
Asp Glu Gly Trp Gly Gly Leu Phe Cys Asp Gln Asp Leu Asn Tyr Cys
        275                 280                 285
Thr His His Ser Pro Cys Lys Asn Gly Ala Thr Cys Ser Asn Ser Gly
    290                 295                 300
Gln Arg Ser Tyr Thr Cys Thr Cys Arg Pro Gly Tyr Thr Gly Val Asp
305                 310                 315                 320
Cys Glu Leu Glu Leu Ser Glu Cys Asp Ser Asn Pro Cys Arg Asn Gly
                325                 330                 335
Gly Ser Cys Lys Asp Gln Glu Asp Gly Tyr His Cys Leu Cys Pro Pro
            340                 345                 350
Gly Tyr Tyr Gly Leu His Cys Glu His Ser Thr Leu Ser Cys Ala Asp
        355                 360                 365
Ser Pro Cys Phe Asn Gly Gly Ser Cys Arg Glu Arg Asn Gln Gly Ala
    370                 375                 380
Asn Tyr Ala Cys Glu Cys Pro Pro Asn Phe Thr Gly Ser Asn Cys Glu
385                 390                 395                 400
Lys Lys Val Asp Arg Cys Thr Ser Asn Pro Cys Ala Asn Gly Gly Gln
                405                 410                 415
Cys Leu Asn Arg Gly Pro Ser Arg Met Cys Arg Cys Arg Pro Gly Phe
            420                 425                 430
Thr Gly Thr Tyr Cys Glu Leu His Val Ser Asp Cys Ala Arg Asn Pro
        435                 440                 445
Cys Ala His Gly Gly Thr Cys His Asp Leu Glu Asn Gly Leu Met Cys
    450                 455                 460
Thr Cys Pro Ala Gly Phe Ser Gly Arg Arg Cys Glu Val Arg Thr Ser
465                 470                 475                 480
Ile Asp Ala Cys Ala Ser Ser Pro Cys Phe Asn Arg Ala Thr Cys Tyr
                485                 490                 495
Thr Asp Leu Ser Thr Asp Thr Phe Val Cys Asn Cys Pro Tyr Gly Phe
            500                 505                 510
Val Gly Ser Arg Cys Glu Phe Pro Val Gly Leu Pro Pro Ser Phe Pro
        515                 520                 525
Trp Val Ala Val Ser Leu Gly Val Gly Leu Ala Val Leu Leu Val Leu
    530                 535                 540
Leu Gly Met Val Ala Val Ala Val Arg Gln Leu Arg Leu Arg Arg Pro
545                 550                 555                 560
Asp Asp Gly Ser Arg Glu Ala Met Asn Asn Leu Ser Asp Phe Gln Lys
                565                 570                 575
Asp Asn Leu Ile Pro Ala Ala Gln Leu Lys Asn Thr Asn Gln Lys Lys
            580                 585                 590
Glu Leu Glu Val Asp Cys Gly Leu Asp Lys Ser Asn Cys Gly Lys Gln
        595                 600                 605
Gln Asn His Thr Leu Asp Tyr Asn Leu Ala Pro Gly Pro Leu Gly Arg
    610                 615                 620
Gly Thr Met Pro Gly Lys Phe Pro His Ser Asp Lys Ser Leu Gly Glu
```

```
                625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
                660                 665                 670

Ser Glu Glu Arg Asn Glu Cys Val Ile Ala Thr Glu Val
                675                 680                 685

<210> SEQ ID NO 3
<211> LENGTH: 372
<212> TYPE: DNA
<213> ORGANISM: Artificial Sequence
<220> FEATURE:
<223> OTHER INFORMATION: Synthetic

<400> SEQUENCE: 3
caggtgcagc tggtgcagtc aggtccagga ctggtgaagc cctcgcagaa cctctcactc      60
acctgtgcca tctccggaga cagtgtctct agtgatagtg ctgcttggaa ctggatcagg     120
cagtccccat cgagaggcct gagtggctgg gaaggacat actacaggtc caagtggtat     180
aatgattatg cagtatctgt gaaaagtcga ataaccttca acccagatac atccaagaac     240
cacatctccc tgcagctgaa ctctgtgact cccgaggaca cggctatcta ttactgtgca     300 agagagggg ataattggaa ttacggctgg ctcgacccct ggggccaggg aaccacggtc      360
accgtctcct ca                                                        372

<210> SEQ ID NO 4
<211> LENGTH: 124
<212> TYPE: PRT
<213> ORGANISM: Artificial Sequence
<220> FEATURE:
<223> OTHER INFORMATION: Synthetic

<400> SEQUENCE: 4

Gln Val Gln Leu Val Gln Ser Gly Pro Gly Leu Val Lys Pro Ser Gln
  1               5                  10                  15

Asn Leu Ser Leu Thr Cys Ala Ile Ser Gly Asp Ser Val Ser Ser Asp
             20                  25                  30

Ser Ala Ala Trp Asn Trp Ile Arg Gln Ser Pro Ser Arg Gly Leu Glu
         35                  40                  45

Trp Leu Gly Arg Thr Tyr Tyr Arg Ser Lys Trp Tyr Asn Asp Tyr Ala
     50                  55                  60

Val Ser Val Lys Ser Arg Ile Thr Phe Asn Pro Asp Thr Ser Lys Asn
 65                  70                  75                  80

His Ile Ser Leu Gln Leu Asn Ser Val Thr Pro Glu Asp Thr Ala Ile
             85                  90                  95

Tyr Tyr Cys Ala Arg Glu Gly Asp Asn Trp Asn Tyr Gly Trp Leu Asp
            100                 105                 110

Pro Trp Gly Gln Gly Thr Thr Val Thr Val Ser Ser
        115                 120

<210> SEQ ID NO 5
<211> LENGTH: 30
<212> TYPE: DNA
<213> ORGANISM: Artificial Sequence
<220> FEATURE:
<223> OTHER INFORMATION: Synthetic

<400> SEQUENCE: 5
ggagacagtg tctctagtga tagtgctgct                                      30
```

<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Gly Asp Ser Val Ser Ser Asp Ser Ala Ala
1               5                   10

<210> SEQ ID NO 7
<211> LENGTH: 27
<212> TYPE: DNA
<213> ORGANISM: Artificial Sequence
<220> FEATURE:
<223> OTHER INFORMATION: Synthetic

<400> SEQUENCE: 7
acatactaca ggtccaagtg gtataat                                          27

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Thr Tyr Tyr Arg Ser Lys Trp Tyr Asn
1               5

<210> SEQ ID NO 9
<211> LENGTH: 42
<212> TYPE: DNA
<213> ORGANISM: Artificial Sequence
<220> FEATURE:
<223> OTHER INFORMATION: Synthetic

<400> SEQUENCE: 9
gcaagagagg gggataattg gaattacggc tggctcgacc cc                         42

<210> SEQ ID NO 10
<211> LENGTH: 14
<212> TYPE: PRT
<213> ORGANISM: Artificial Sequence
<220> FEATURE:
<223> OTHER INFORMATION: Synthetic

<400> SEQUENCE: 10

Ala Arg Glu Gly Asp Asn Trp Asn Tyr Gly Trp Leu Asp Pro
1               5                   10

<210> SEQ ID NO 11
<211> LENGTH: 336
<212> TYPE: DNA
<213> ORGANISM: Artificial Sequence
<220> FEATURE:
<223> OTHER INFORMATION: Synthetic

<400> SEQUENCE: 11
gacatccagt tgacccagtc tccactctcc ctgcccgtca cccctggaga gccggcctcc      60
atctcctgca ggtctagtca gagcctcctt cttagtaatg gatacaacta tttggattgg     120
tacctgcaga agccagggca gtctccacaa ctcctgatct atttggtttc tagtcgggcc     180

```
tccggggtcc ctgacaggtt cagtggcagt ggatccggca cagattttac actgaaaatc    240
agcagagtgg aggctgagga ttttggaatt tattattgta tgcaagctct acaaactccg    300
tacacttttg gccgggggac caaggtggaa atcaaa                              336
```

<210> SEQ ID NO 12
<211> LENGTH: 112
<212> TYPE: PRT
<213> ORGANISM: Artificial Sequence
<220> FEATURE:
<223> OTHER INFORMATION: Synthetic

<400> SEQUENCE: 12

```
Asp Ile Gln Leu Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Leu Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Val Ser Ser Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Phe Gly Ile Tyr Tyr Cys Met Gln Ala
                85                  90                  95

Leu Gln Thr Pro Tyr Thr Phe Gly Arg Gly Thr Lys Val Glu Ile Lys
            100                 105                 110
```

<210> SEQ ID NO 13
<211> LENGTH: 33
<212> TYPE: DNA
<213> ORGANISM: Artificial Sequence
<220> FEATURE:
<223> OTHER INFORMATION: Synthetic

<400> SEQUENCE: 13

```
cagagcctcc ttcttagtaa tggatacaac tat                                 33
```

<210> SEQ ID NO 14
<211> LENGTH: 11
<212> TYPE: PRT
<213> ORGANISM: Artificial Sequence
<220> FEATURE:
<223> OTHER INFORMATION: Synthetic

<400> SEQUENCE: 14

```
Gln Ser Leu Leu Leu Ser Asn Gly Tyr Asn Tyr
 1               5                  10
```

<210> SEQ ID NO 15
<211> LENGTH: 9
<212> TYPE: DNA
<213> ORGANISM: Artificial Sequence
<220> FEATURE:
<223> OTHER INFORMATION: Synthetic

<400> SEQUENCE: 15

```
ttggtttct                                                             9
```

<210> SEQ ID NO 16
<211> LENGTH: 3
<212> TYPE: PRT
<213> ORGANISM: Artificial Sequence
<220> FEATURE:

```
<223> OTHER INFORMATION: Synthetic

<400> SEQUENCE: 16

Leu Val Ser
  1

<210> SEQ ID NO 17
<211> LENGTH: 27
<212> TYPE: DNA
<213> ORGANISM: Artificial Sequence
<220> FEATURE:
<223> OTHER INFORMATION: Synthetic

<400> SEQUENCE: 17
atgcaagctc tacaaactcc gtacact                                          27

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Met Gln Ala Leu Gln Thr Pro Tyr Thr
  1               5

<210> SEQ ID NO 19
<211> LENGTH: 369
<212> TYPE: DNA
<213> ORGANISM: Artificial Sequence
<220> FEATURE:
<223> OTHER INFORMATION: Synthetic

<400> SEQUENCE: 19
gaggtgcagc tggtgcagtc tgggggaggc gtggtccagc ctggagggtc cctgagactc       60
tcctgtgcag cgtctggatt caccttcagt agttatggca tgcactgggt ccgccaggct     120
ccaggcaagg ggctggagtg ggtgtcattt ttatggtatg atggaactaa taaaaactat     180
gtagagtccg tgaagggccg attcaccatc tcaagagaca attccaagaa tatgctgtat     240
ctggaaatga acagcctgag agccgaggac acggctgtgt attactgtgc gagagatcac     300
gattttagga gtggttatga ggggtggttc gacccctggg gccagggaac cctggtcacc     360
gtctcctca                                                             369

<210> SEQ ID NO 20
<211> LENGTH: 123
<212> TYPE: PRT
<213> ORGANISM: Artificial Sequence
<220> FEATURE:
<223> OTHER INFORMATION: Synthetic

<400> SEQUENCE: 20

Glu Val Gln Leu Val Gln Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ser Phe Leu Trp Tyr Asp Gly Thr Asn Lys Asn Tyr Val Glu Ser Val
     50                  55                  60

Lys Gly Arg Phe Thr Ile Ser Arg Asp Asn Ser Lys Asn Met Leu Tyr
 65                  70                  75                  80
```

Leu Glu Met Asn Ser Leu Arg Ala Glu Asp Thr Ala Val Tyr Tyr Cys
            85                  90                  95

Ala Arg Asp His Asp Phe Arg Ser Gly Tyr Glu Gly Trp Phe Asp Pro
        100                 105                 110

Trp Gly Gln Gly Thr Leu Val Thr Val Ser Ser
        115                 120

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
ggattcacct tcagtagtta tggc                                          24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Gly Phe Thr Phe Ser Ser Tyr Gly
 1               5

<210> SEQ ID NO 23
<211> LENGTH: 24
<212> TYPE: DNA
<213> ORGANISM: Artificial Sequence
<220> FEATURE:
<223> OTHER INFORMATION: Synthetic

<400> SEQUENCE: 23
ttatggtatg atggaactaa taaa                                          24

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Leu Trp Tyr Asp Gly Thr Asn Lys
 1               5

<210> SEQ ID NO 25
<211> LENGTH: 48
<212> TYPE: DNA
<213> ORGANISM: Artificial Sequence
<220> FEATURE:
<223> OTHER INFORMATION: Synthetic

<400> SEQUENCE: 25
gcgagagatc acgattttag gagtggttat gaggggtggt tcgacccc                48

<210> SEQ ID NO 26
<211> LENGTH: 16
<212> TYPE: PRT
<213> ORGANISM: Artificial Sequence
<220> FEATURE:
<223> OTHER INFORMATION: Synthetic

```
<400> SEQUENCE: 26

Ala Arg Asp His Asp Phe Arg Ser Gly Tyr Glu Gly Trp Phe Asp Pro
 1               5                  10                  15

<210> SEQ ID NO 27
<211> LENGTH: 321
<212> TYPE: DNA
<213> ORGANISM: Artificial Sequence
<220> FEATURE:
<223> OTHER INFORMATION: Synthetic

<400> SEQUENCE: 27
gaaatagtga tgacacagtc tccagccacc ctgtctttgt ctccagggga aagagccacc     60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcaacac cgtagcaact ggcctcccac tttcggcgga    300
gggaccaagg tggaaatcaa a                                              321

<210> SEQ ID NO 28
<211> LENGTH: 107
<212> TYPE: PRT
<213> ORGANISM: Artificial Sequence
<220> FEATURE:
<223> OTHER INFORMATION: Synthetic

<400> SEQUENCE: 28

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Ser Asn Trp Pro Pro
                85                  90                  95

Thr Phe Gly Gly Gly Thr Lys Val Glu Ile Lys
            100                 105

<210> SEQ ID NO 29
<211> LENGTH: 18
<212> TYPE: DNA
<213> ORGANISM: Artificial Sequence
<220> FEATURE:
<223> OTHER INFORMATION: Synthetic

<400> SEQUENCE: 29
cagagtgtta gcagctac                                                   18

<210> SEQ ID NO 30
<211> LENGTH: 6
<212> TYPE: PRT
<213> ORGANISM: Artificial Sequence
<220> FEATURE:
<223> OTHER INFORMATION: Synthetic

<400> SEQUENCE: 30
```

Gln Ser Val Ser Ser Tyr
 1               5

<210> SEQ ID NO 31
<211> LENGTH: 9
<212> TYPE: DNA
<213> ORGANISM: Artificial Sequence
<220> FEATURE:
<223> OTHER INFORMATION: Synthetic

<400> SEQUENCE: 31 gatgcatcc                                                                9

<210> SEQ ID NO 32
<211> LENGTH: 3
<212> TYPE: PRT
<213> ORGANISM: Artificial Sequence
<220> FEATURE:
<223> OTHER INFORMATION: Synthetic

<400> SEQUENCE: 32

Asp Ala Ser
 1

<210> SEQ ID NO 33
<211> LENGTH: 27
<212> TYPE: DNA
<213> ORGANISM: Artificial Sequence
<220> FEATURE:
<223> OTHER INFORMATION: Synthetic

<400> SEQUENCE: 33
caacaccgta gcaactggcc tcccact                                           27

<210> SEQ ID NO 34
<211> LENGTH: 9
<212> TYPE: PRT
<213> ORGANISM: Artificial Sequence
<220> FEATURE:
<223> OTHER INFORMATION: Synthetic

<400> SEQUENCE: 34

Gln His Arg Ser Asn Trp Pro Pro Thr
 1               5

<210> SEQ ID NO 35
<211> LENGTH: 357
<212> TYPE: DNA
<213> ORGANISM: Artificial Sequence
<220> FEATURE:
<223> OTHER INFORMATION: Synthetic

<400> SEQUENCE: 35
caggtgcagc tgcaggagtc gggcccagga ctggtgaagc cttcacagac cctgtccctc        60
acctgcactg tctctgatgg ctccatcaac agtgttgaat cctactggac ctggatccgc       120
cagcacccag ggaagggcct ggagtggatt ggatacatca aatacactgg gggcatccac       180
tataacccgt ccctcaagag tcgacttgcc atatcagtgg acacgtcaaa gaaccagttc       240
tccctgaaaa tgagctctgt gactgccgcg gacacggccg tgtattactg tgcgagagca       300
cgtggaagtc atactttga tgtctggggc caggggacaa tggtcaccgt ctcttca          357

<210> SEQ ID NO 36
<211> LENGTH: 119
<212> TYPE: PRT
<213> ORGANISM: Artificial Sequence -continued

```
<220> FEATURE:
<223> OTHER INFORMATION: Synthetic

<400> SEQUENCE: 36

Gln Val Gln Leu Gln Glu Ser Gly Pro Gly Leu Val Lys Pro Ser Gln
  1               5                  10                  15

Thr Leu Ser Leu Thr Cys Thr Val Ser Asp Gly Ser Ile Asn Ser Val
             20                  25                  30

Glu Ser Tyr Trp Thr Trp Ile Arg Gln His Pro Gly Lys Gly Leu Glu
         35                  40                  45

Trp Ile Gly Tyr Ile Lys Tyr Thr Gly Gly Ile His Tyr Asn Pro Ser
 50                  55                  60

Leu Lys Ser Arg Leu Ala Ile Ser Val Asp Thr Ser Lys Asn Gln Phe
65                  70                  75                  80

Ser Leu Lys Met Ser Ser Val Thr Ala Ala Asp Thr Ala Val Tyr Tyr
             85                  90                  95

Cys Ala Arg Ala Arg Gly Ser His Thr Phe Asp Val Trp Gly Gln Gly
            100                 105                 110

Thr Met Val Thr Val Ser Ser
            115

<210> SEQ ID NO 37
<211> LENGTH: 30
<212> TYPE: DNA
<213> ORGANISM: Artificial Sequence
<220> FEATURE:
<223> OTHER INFORMATION: Synthetic

<400> SEQUENCE: 37
gatggctcca tcaacagtgt tgaatcctac                                          30

<210> SEQ ID NO 38
<211> LENGTH: 10
<212> TYPE: PRT
<213> ORGANISM: Artificial Sequence
<220> FEATURE:
<223> OTHER INFORMATION: Synthetic

<400> SEQUENCE: 38

Asp Gly Ser Ile Asn Ser Val Glu Ser Tyr
  1               5                  10

<210> SEQ ID NO 39
<211> LENGTH: 21
<212> TYPE: DNA
<213> ORGANISM: Artificial Sequence
<220> FEATURE:
<223> OTHER INFORMATION: Synthetic

<400> SEQUENCE: 39
atcaaataca ctgggggcat c                                                   21

<210> SEQ ID NO 40
<211> LENGTH: 7
<212> TYPE: PRT
<213> ORGANISM: Artificial Sequence
<220> FEATURE:
<223> OTHER INFORMATION: Synthetic

<400> SEQUENCE: 40

Ile Lys Tyr Thr Gly Gly Ile
  1               5
```

<210> SEQ ID NO 41
<211> LENGTH: 33
<212> TYPE: DNA
<213> ORGANISM: Artificial Sequence
<220> FEATURE:
<223> OTHER INFORMATION: Synthetic

<400> SEQUENCE: 41
gcgagagcac gtggaagtca tactttgat gtc          33

<210> SEQ ID NO 42
<211> LENGTH: 11
<212> TYPE: PRT
<213> ORGANISM: Artificial Sequence
<220> FEATURE:
<223> OTHER INFORMATION: Synthetic

<400> SEQUENCE: 42

Ala Arg Ala Arg Gly Ser His Thr Phe Asp Val
 1               5                  10

<210> SEQ ID NO 43
<211> LENGTH: 324
<212> TYPE: DNA
<213> ORGANISM: Artificial Sequence
<220> FEATURE:
<223> OTHER INFORMATION: Synthetic

<400> SEQUENCE: 43
gaaattgtgc tgactcagtc tccaggcacc ctgtcttggt ctccagggga aagagccacc          60
ctctcctgca gggccagtca gagtattagc agtaactact tagcctggta ccagcagaaa         120
cctggccagg ctcccagact cctcatttat ggtgcatcca gcagggtcac tggcatccca         180
gacaggttca gtggcagtgg gtctgggaca gacttcactc tcaccatcag cagactggag         240
cctgaagatt ttgcactgta ttattgtcag cagtatagta ggtcaccgat caccttcggc         300
caagggacca aagtggatat caaa                                                324

<210> SEQ ID NO 44
<211> LENGTH: 108
<212> TYPE: PRT
<213> ORGANISM: Artificial Sequence
<220> FEATURE:
<223> OTHER INFORMATION: Synthetic

<400> SEQUENCE: 44

Glu Ile Val Leu Thr Gln Ser Pro Gly Thr Leu Ser Trp Ser Pro Gly
 1               5                  10                  15

Glu Arg Ala Thr Leu Ser Cys Arg Ala Ser Gln Ser Ile Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Val Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Leu Tyr Tyr Cys Gln Gln Tyr Ser Arg Ser Pro
                85                  90                  95

Ile Thr Phe Gly Gln Gly Thr Lys Val Asp Ile Lys
            100                 105

<210> SEQ ID NO 45
<211> LENGTH: 21

```
<212> TYPE: DNA
<213> ORGANISM: Artificial Sequence
<220> FEATURE:
<223> OTHER INFORMATION: Synthetic

<400> SEQUENCE: 45
cagagtatta gcagtaacta c                                            21

<210> SEQ ID NO 46
<211> LENGTH: 7
<212> TYPE: PRT
<213> ORGANISM: Artificial Sequence
<220> FEATURE:
<223> OTHER INFORMATION: Synthetic

<400> SEQUENCE: 46

Gln Ser Ile Ser Ser Asn Tyr
 1               5

<210> SEQ ID NO 47
<211> LENGTH: 9
<212> TYPE: DNA
<213> ORGANISM: Artificial Sequence
<220> FEATURE:
<223> OTHER INFORMATION: Synthetic

<400> SEQUENCE: 47 ggtgcatcc                                                           9

<210> SEQ ID NO 48
<211> LENGTH: 3
<212> TYPE: PRT
<213> ORGANISM: Artificial Sequence
<220> FEATURE:
<223> OTHER INFORMATION: Synthetic

<400> SEQUENCE: 48

Gly Ala Ser
 1

<210> SEQ ID NO 49
<211> LENGTH: 27
<212> TYPE: DNA
<213> ORGANISM: Artificial Sequence
<220> FEATURE:
<223> OTHER INFORMATION: Synthetic

<400> SEQUENCE: 49
cagcagtata gtaggtcacc gatcacc                                       27

<210> SEQ ID NO 50
<211> LENGTH: 9
<212> TYPE: PRT
<213> ORGANISM: Artificial Sequence
<220> FEATURE:
<223> OTHER INFORMATION: Synthetic

<400> SEQUENCE: 50

Gln Gln Tyr Ser Arg Ser Pro Ile Thr
 1               5

<210> SEQ ID NO 51
<211> LENGTH: 357
<212> TYPE: DNA
<213> ORGANISM: Artificial Sequence
<220> FEATURE:
<223> OTHER INFORMATION: Synthetic
```

<400> SEQUENCE: 51

```
caggtgcagc tgcaggagtc gggcccagga ctggtgaagc cttcacagac cctgtccctc      60
acctgcactg tctctggtgg ctccatcaac agtgttactt actactggac ctggatccgc     120
cagcacccag gaggggcct agagtggatt gggtacatca aattcagtgg agcacctac       180
tacaacccgt ccctcaaggg tcgagtcacc atatcagtgg acacgtctaa gaaccaattc     240
tcccttaaaa ttaactctgt gactgccgcg gacacggccg tgttttactg tgcgagagct     300
tctggaagtc atactttga tatctgggc caagggacaa tggtcaccgt ctcctca          357
```

<210> SEQ ID NO 52
<211> LENGTH: 119
<212> TYPE: PRT
<213> ORGANISM: Artificial Sequence
<220> FEATURE:
<223> OTHER INFORMATION: Synthetic

<400> SEQUENCE: 52

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Asn Ser Val
            20                  25                  30

Thr Tyr Tyr Trp Thr Trp Ile Arg Gln His Pro Gly Arg Gly Leu Glu
        35                  40                  45

Trp Ile Gly Tyr Ile Lys Phe Ser Gly Ser Thr Tyr Tyr Asn Pro Ser
    50                  55                  60

Leu Lys Gly Arg Val Thr Ile Ser Val Asp Thr Ser Lys Asn Gln Phe
65                  70                  75                  80

Ser Leu Lys Ile Asn Ser Val Thr Ala Ala Asp Thr Ala Val Phe Tyr
                85                  90                  95

Cys Ala Arg Ala Ser Gly Ser His Thr Phe Asp Ile Trp Gly Gln Gly
            100                 105                 110

Thr Met Val Thr Val Ser Ser
        115
```

<210> SEQ ID NO 53
<211> LENGTH: 30
<212> TYPE: DNA
<213> ORGANISM: Artificial Sequence
<220> FEATURE:
<223> OTHER INFORMATION: Synthetic

<400> SEQUENCE: 53

```
ggtggctcca tcaacagtgt tacttactac                                       30
```

<210> SEQ ID NO 54
<211> LENGTH: 10
<212> TYPE: PRT
<213> ORGANISM: Artificial Sequence
<220> FEATURE:
<223> OTHER INFORMATION: Synthetic

<400> SEQUENCE: 54

```
Gly Gly Ser Ile Asn Ser Val Thr Tyr Tyr
 1               5                  10
```

<210> SEQ ID NO 55
<211> LENGTH: 21
<212> TYPE: DNA
<213> ORGANISM: Artificial Sequence
<220> FEATURE:
<223> OTHER INFORMATION: Synthetic -continued
<210> SEQ ID NO 55
<211> LENGTH: 21
<212> TYPE: DNA
<213> ORGANISM: Artificial Sequence
<220> FEATURE:
<223> OTHER INFORMATION: Synthetic

<400> SEQUENCE: 55
atcaaattca gtgggagcac c                                              21

<210> SEQ ID NO 56
<211> LENGTH: 7
<212> TYPE: PRT
<213> ORGANISM: Artificial Sequence
<220> FEATURE:
<223> OTHER INFORMATION: Synthetic

<400> SEQUENCE: 56

Ile Lys Phe Ser Gly Ser Thr
 1               5

<210> SEQ ID NO 57
<211> LENGTH: 33
<212> TYPE: DNA
<213> ORGANISM: Artificial Sequence
<220> FEATURE:
<223> OTHER INFORMATION: Synthetic

<400> SEQUENCE: 57
gcgagagctt ctggaagtca tactttttgat atc                                33

<210> SEQ ID NO 58
<211> LENGTH: 11
<212> TYPE: PRT
<213> ORGANISM: Artificial Sequence
<220> FEATURE:
<223> OTHER INFORMATION: Synthetic

<400> SEQUENCE: 58

Ala Arg Ala Ser Gly Ser His Thr Phe Asp Ile
 1               5                  10

<210> SEQ ID NO 59
<211> LENGTH: 324
<212> TYPE: DNA
<213> ORGANISM: Artificial Sequence
<220> FEATURE:
<223> OTHER INFORMATION: Synthetic

<400> SEQUENCE: 59
gaaacgacac tcacgcagtc tccaggcacc ctgtctttgt ctccagggga aagagccacc    60
ctctcctgca gggccagtca gagtgttagc aacagctact tagcctggta ccagcagaaa   120
cctggccagg ctcccaggct cctcatctct ggtgcgtcca gcagggtcac tggcatccca   180
gacaggttca gtggcagtgg gtctgggaca gacttcactc tcaccatcag cagactggag   240
cctgaagatt ttggaatgta ttactgtcag cagtatagta ggtcaccgat caccttcggc   300
caagggacca agctggagat caaa                                           324

<210> SEQ ID NO 60
<211> LENGTH: 108
<212> TYPE: PRT
<213> ORGANISM: Artificial Sequence
<220> FEATURE:
<223> OTHER INFORMATION: Synthetic

<400> SEQUENCE: 60

Glu Thr Thr Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Asn Ser
            20                  25                  30

```
Tyr Leu Ala Trp Tyr Gln Gln Lys Pro Gly Gln Ala Pro Arg Leu Leu
            35                  40                  45

Ile Ser Gly Ala Ser Ser Arg Val Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Gly Met Tyr Tyr Cys Gln Gln Tyr Ser Arg Ser Pro
                 85                  90                  95

Ile Thr Phe Gly Gln Gly Thr Lys Leu Glu Ile Lys
            100                 105

<210> SEQ ID NO 61
<211> LENGTH: 21
<212> TYPE: DNA
<213> ORGANISM: Artificial Sequence
<220> FEATURE:
<223> OTHER INFORMATION: Synthetic

<400> SEQUENCE: 61
cagagtgtta gcaacagcta c                                          21

<210> SEQ ID NO 62
<211> LENGTH: 7
<212> TYPE: PRT
<213> ORGANISM: Artificial Sequence
<220> FEATURE:
<223> OTHER INFORMATION: Synthetic

<400> SEQUENCE: 62

Gln Ser Val Ser Asn Ser Tyr
 1               5

<210> SEQ ID NO 63
<211> LENGTH: 9
<212> TYPE: DNA
<213> ORGANISM: Artificial Sequence
<220> FEATURE:
<223> OTHER INFORMATION: Synthetic

<400> SEQUENCE: 63 ggtgcgtcc                                                         9

<210> SEQ ID NO 64
<211> LENGTH: 3
<212> TYPE: PRT
<213> ORGANISM: Artificial Sequence
<220> FEATURE:
<223> OTHER INFORMATION: Synthetic

<400> SEQUENCE: 64

Gly Ala Ser
 1

<210> SEQ ID NO 65
<211> LENGTH: 27
<212> TYPE: DNA
<213> ORGANISM: Artificial Sequence
<220> FEATURE:
<223> OTHER INFORMATION: Synthetic

<400> SEQUENCE: 65
cagcagtata gtaggtcacc gatcacc                                     27

<210> SEQ ID NO 66
```

```
<211> LENGTH: 9
<212> TYPE: PRT
<213> ORGANISM: Artificial Sequence
<220> FEATURE:
<223> OTHER INFORMATION: Synthetic

<400> SEQUENCE: 66

Gln Gln Tyr Ser Arg Ser Pro Ile Thr
 1               5

<210> SEQ ID NO 67
<211> LENGTH: 360
<212> TYPE: DNA
<213> ORGANISM: Artificial Sequence
<220> FEATURE:
<223> OTHER INFORMATION: Synthetic

<400> SEQUENCE: 67
gaagtgcagc tggtgcagtc tgggggagcc ttggtacaac ctgggggggtc cctgagactc      60 tcctgtgcag cctctggatt cacctttaac aactttgcca tgacctgggt ccgccaggct     120
ccagggaagg gcctggagtg ggtctcaact attagtggta gtggcgttga cacatactgc     180
gcagactccg tgaagggccg gttcaccatc tccagagaca attccaagaa cacactgtat     240
ctgcaaatga acagcctgag agccgaggac acggccgtat attactgttc gaaagatggc     300
gccttctata gtggctacga acactactgg ggccagggaa ccacggtcac cgtctcctca     360

<210> SEQ ID NO 68
<211> LENGTH: 120
<212> TYPE: PRT
<213> ORGANISM: Artificial Sequence
<220> FEATURE:
<223> OTHER INFORMATION: Synthetic

<400> SEQUENCE: 68

Glu Val Gln Leu Val Gln Ser Gly Gly Ala Leu Val Gln Pro Gly Gly
 1               5                  10                  15

Ser Leu Arg Leu Ser Cys Ala Ala Ser Gly Phe Thr Phe Asn Asn Phe
            20                  25                  30

Ala Met Thr Trp Val Arg Gln Ala Pro Gly Lys Gly Leu Glu Trp Val
        35                  40                  45

Ser Thr Ile Ser Gly Ser Gly Val Asp Thr Tyr Cys Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Lys Asp Gly Ala Phe Tyr Ser Gly Tyr Glu His Tyr Trp Gly Gln
            100                 105                 110

Gly Thr Thr Val Thr Val Ser Ser
        115                 120

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
ggattcacct ttaacaactt tgcc                                              24
```

```
<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Gly Phe Thr Phe Asn Asn Phe Ala
 1               5

<210> SEQ ID NO 71
<211> LENGTH: 24
<212> TYPE: DNA
<213> ORGANISM: Artificial Sequence
<220> FEATURE:
<223> OTHER INFORMATION: Synthetic

<400> SEQUENCE: 71
attagtggta gtggcgttga caca                                              24

<210> SEQ ID NO 72
<211> LENGTH: 8
<212> TYPE: PRT
<213> ORGANISM: Artificial Sequence
<220> FEATURE:
<223> OTHER INFORMATION: Synthetic

<400> SEQUENCE: 72

Ile Ser Gly Ser Gly Val Asp Thr
 1               5

<210> SEQ ID NO 73
<211> LENGTH: 39
<212> TYPE: DNA
<213> ORGANISM: Artificial Sequence
<220> FEATURE:
<223> OTHER INFORMATION: Synthetic

<400> SEQUENCE: 73
tcgaaagatg gcgccttcta tagtggctac gaacactac                              39

<210> SEQ ID NO 74
<211> LENGTH: 13
<212> TYPE: PRT
<213> ORGANISM: Artificial Sequence
<220> FEATURE:
<223> OTHER INFORMATION: Synthetic

<400> SEQUENCE: 74

Ser Lys Asp Gly Ala Phe Tyr Ser Gly Tyr Glu His Tyr
 1               5                   10

<210> SEQ ID NO 75
<211> LENGTH: 324
<212> TYPE: DNA
<213> ORGANISM: Artificial Sequence
<220> FEATURE:
<223> OTHER INFORMATION: Synthetic

<400> SEQUENCE: 75
gaaacgacac tcacgcagtc tccaggcacc ctgtctttgt ctccagggga aagagccacc        60
ctctcctgca gggccagtca gagtgttagc agcagctact tagcctggta ccagcagaaa       120
cctggccagg ctcccaggct cctcatctat ggtacatcca acagggccac tggcatccca       180
gacaggttca gtggcagtgg gtctgggaca gacttcactc tcaccatcag cagactggag       240
```
tctgaagatt ttgcagtgta ttactgtcag cagtatggta gctcacctcg gacgttcggc    300
caagggacca aggtggagat caaa    324

<210> SEQ ID NO 76
<211> LENGTH: 108
<212> TYPE: PRT
<213> ORGANISM: Artificial Sequence
<220> FEATURE:
<223> OTHER INFORMATION: Synthetic

<400> SEQUENCE: 76

Glu Thr Thr Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Thr Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Ser Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys
            100                 105

<210> SEQ ID NO 77
<211> LENGTH: 21
<212> TYPE: DNA
<213> ORGANISM: Artificial Sequence
<220> FEATURE:
<223> OTHER INFORMATION: Synthetic

<400> SEQUENCE: 77
cagagtgtta gcagcagcta c    21

<210> SEQ ID NO 78
<211> LENGTH: 7
<212> TYPE: PRT
<213> ORGANISM: Artificial Sequence
<220> FEATURE:
<223> OTHER INFORMATION: Synthetic

<400> SEQUENCE: 78

Gln Ser Val Ser Ser Ser Tyr
 1               5

<210> SEQ ID NO 79
<211> LENGTH: 9
<212> TYPE: DNA
<213> ORGANISM: Artificial Sequence
<220> FEATURE:
<223> OTHER INFORMATION: Synthetic

<400> SEQUENCE: 79 ggtacatcc    9

<210> SEQ ID NO 80
<211> LENGTH: 3
<212> TYPE: PRT
<213> ORGANISM: Artificial Sequence
<220> FEATURE:
<223> OTHER INFORMATION: Synthetic

<400> SEQUENCE: 80

Gly Thr Ser
 1

<210> SEQ ID NO 81
<211> LENGTH: 27
<212> TYPE: DNA
<213> ORGANISM: Artificial Sequence
<220> FEATURE:
<223> OTHER INFORMATION: Synthetic

<400> SEQUENCE: 81
cagcagtatg gtagctcacc tcggacg                                         27

<210> SEQ ID NO 82
<211> LENGTH: 9
<212> TYPE: PRT
<213> ORGANISM: Artificial Sequence
<220> FEATURE:
<223> OTHER INFORMATION: Synthetic

<400> SEQUENCE: 82

Gln Gln Tyr Gly Ser Ser Pro Arg Thr
 1               5

<210> SEQ ID NO 83
<211> LENGTH: 357
<212> TYPE: DNA
<213> ORGANISM: Artificial Sequence
<220> FEATURE:
<223> OTHER INFORMATION: Synthetic

<400> SEQUENCE: 83
gaagtgcagc tggtgcagtc tggacctgag gtgaagaagc ctggggcctc agtgaaggtc      60
tcctgcaagg cttctggtta cacctttacc tactatggta tcagttggat acgacagacc     120
cctggacaag gcttgagtg gatgggatgg atcagcgctt acgatggtaa cacagactat     180
gcacagaagt tccaagacag aatcaccatg accacagaca catcctcgac cacagcctac     240
atggaactga ggagcctgag atctgacgac acggccgtct attactgtgc gaggtatagt     300
tggaacaagc actggttcga cccctggggc cagggaacca tggtcaccgt ctcttca       357

<210> SEQ ID NO 84
<211> LENGTH: 119
<212> TYPE: PRT
<213> ORGANISM: Artificial Sequence
<220> FEATURE:
<223> OTHER INFORMATION: Synthetic

<400> SEQUENCE: 84

Glu Val Gln Leu Val Gln Ser Gly Pro Glu Val Lys Lys Pro Gly Ala
 1               5                  10                  15

Ser Val Lys Val Ser Cys Lys Ala Ser Gly Tyr Thr Phe Thr Tyr Tyr
             20                  25                  30

Gly Ile Ser Trp Ile Arg Gln Thr Pro Gly Gln Gly Leu Glu Trp Met
         35                  40                  45

Gly Trp Ile Ser Ala Tyr Asp Gly Asn Thr Asp Tyr Ala Gln Lys Phe
     50                  55                  60

Gln Asp Arg Ile Thr Met Thr Thr Asp Thr Ser Thr Thr Ala Tyr
 65                  70                  75                  80

Met Glu Leu Arg Ser Leu Arg Ser Asp Asp Thr Ala Val Tyr Tyr Cys
                 85                  90                  95

Ala Arg Tyr Ser Trp Asn Lys His Trp Phe Asp Pro Trp Gly Gln Gly
            100                 105                 110
Thr Met Val Thr Val Ser Ser
            115

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
ggttacacct ttacctacta tggt                                           24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Gly Tyr Thr Phe Thr Tyr Tyr Gly
1               5

<210> SEQ ID NO 87
<211> LENGTH: 24
<212> TYPE: DNA
<213> ORGANISM: Artificial Sequence
<220> FEATURE:
<223> OTHER INFORMATION: Synthetic

<400> SEQUENCE: 87
atcagcgctt acgatggtaa caca                                           24

<210> SEQ ID NO 88
<211> LENGTH: 8
<212> TYPE: PRT
<213> ORGANISM: Artificial Sequence
<220> FEATURE:
<223> OTHER INFORMATION: Synthetic

<400> SEQUENCE: 88

Ile Ser Ala Tyr Asp Gly Asn Thr
1               5

<210> SEQ ID NO 89
<211> LENGTH: 36
<212> TYPE: DNA
<213> ORGANISM: Artificial Sequence
<220> FEATURE:
<223> OTHER INFORMATION: Synthetic

<400> SEQUENCE: 89
gcgaggtata gttggaacaa gcactggttc gacccc                              36

<210> SEQ ID NO 90
<211> LENGTH: 12
<212> TYPE: PRT
<213> ORGANISM: Artificial Sequence
<220> FEATURE:
<223> OTHER INFORMATION: Synthetic

<400> SEQUENCE: 90

Ala Arg Tyr Ser Trp Asn Lys His Trp Phe Asp Pro
1               5                   10

<210> SEQ ID NO 91
<211> LENGTH: 324
<212> TYPE: DNA
<213> ORGANISM: Artificial Sequence
<220> FEATURE:
<223> OTHER INFORMATION: Synthetic

<400> SEQUENCE: 91

```
gaaattgtga tgacacagtc tccaggcacc ctgtctttgt ctccagggga cagagccacc      60
ctctcctgca gggccagtca gagtgttacc ggcagctact tagcctggta ccagcagaaa     120
cctggccagg ctcccagact cctcatctat ggtgcatcca acagggccac tggcatccca     180
gacaggttca ctggcagtgg gtctgggaca gacttcactc tcaccatcag cagactggag     240
cctgaagatt ttgcagtgta tttctgtcaa cagtctgctt tctcaccgtg gacgttcggc     300
caggggacca aggtggaaat caaa                                           324
```

<210> SEQ ID NO 92
<211> LENGTH: 108
<212> TYPE: PRT
<213> ORGANISM: Artificial Sequence
<220> FEATURE:
<223> OTHER INFORMATION: Synthetic

<400> SEQUENCE: 92

```
Glu Ile Val Met Thr Gln Ser Pro Gly Thr Leu Ser Leu Ser Pro Gly
  1               5                  10                  15

Asp Arg Ala Thr Leu Ser Cys Arg Ala Ser Gln Ser Val Thr Gly Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Asn Arg Ala Thr Gly Ile Pro Asp Arg Phe Thr
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Phe Cys Gln Gln Ser Ala Phe Ser Pro
                 85                  90                  95

Trp Thr Phe Gly Gln Gly Thr Lys Val Glu Ile Lys
            100                 105
```

<210> SEQ ID NO 93
<211> LENGTH: 21
<212> TYPE: DNA
<213> ORGANISM: Artificial Sequence
<220> FEATURE:
<223> OTHER INFORMATION: Synthetic

<400> SEQUENCE: 93

```
cagagtgtta ccggcagcta c                                              21
```

<210> SEQ ID NO 94
<211> LENGTH: 7
<212> TYPE: PRT
<213> ORGANISM: Artificial Sequence
<220> FEATURE:
<223> OTHER INFORMATION: Synthetic

<400> SEQUENCE: 94

```
Gln Ser Val Thr Gly Ser Tyr
  1               5
```

```
<210> SEQ ID NO 95
<211> LENGTH: 9
<212> TYPE: DNA
<213> ORGANISM: Artificial Sequence
<220> FEATURE:
<223> OTHER INFORMATION: Synthetic

<400> SEQUENCE: 95 ggtgcatcc                                                              9

<210> SEQ ID NO 96
<211> LENGTH: 3
<212> TYPE: PRT
<213> ORGANISM: Artificial Sequence
<220> FEATURE:
<223> OTHER INFORMATION: Synthetic

<400> SEQUENCE: 96

Gly Ala Ser
 1

<210> SEQ ID NO 97
<211> LENGTH: 27
<212> TYPE: DNA
<213> ORGANISM: Artificial Sequence
<220> FEATURE:
<223> OTHER INFORMATION: Synthetic

<400> SEQUENCE: 97
caacagtctg ctttctcacc gtggacg                                          27

<210> SEQ ID NO 98
<211> LENGTH: 9
<212> TYPE: PRT
<213> ORGANISM: Artificial Sequence
<220> FEATURE:
<223> OTHER INFORMATION: Synthetic

<400> SEQUENCE: 98

Gln Gln Ser Ala Phe Ser Pro Trp Thr
 1               5

<210> SEQ ID NO 99
<211> LENGTH: 363
<212> TYPE: DNA
<213> ORGANISM: Artificial Sequence
<220> FEATURE:
<223> OTHER INFORMATION: Synthetic

<400> SEQUENCE: 99
caggtgcagc tgcaggagtc gggcccagga ctggtgaagc cttcacagac cctgtccctc       60
acctgcactg tctctggtgg ctccatcagc agtggtggtt actactggag ttggatccgc      120
cagcacccag ggaagggcct ggagtggatt gggtacatcc attatagtgg gaacacccac      180
tacaatccga ccctcaagag tcgaattacc atatcagtag acacgtctaa gaaccagttc      240
tcccttgagg tgaactctgt gactgccgcg gacacggccg tatactactg tgcgaggaat      300
atggttcggg gagttcactg gttcgacccc tggggccagg gaaccacggt caccgtctcc      360
tca                                                                   363

<210> SEQ ID NO 100
<211> LENGTH: 121
<212> TYPE: PRT
<213> ORGANISM: Artificial Sequence
<220> FEATURE:
<223> OTHER INFORMATION: Synthetic
```

<400> SEQUENCE: 100

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile His Tyr Ser Gly Asn Thr His Tyr Asn Pro Thr
50                  55                  60

Leu Lys Ser Arg Ile Thr Ile Ser Val Asp Thr Ser Lys Asn Gln Phe
65                  70                  75                  80

Ser Leu Glu Val Asn Ser Val Thr Ala Ala Asp Thr Ala Val Tyr Tyr
                85                  90                  95

Cys Ala Arg Asn Met Val Arg Gly Val His Trp Phe Asp Pro Trp Gly
            100                 105                 110

Gln Gly Thr Thr Val Thr Val Ser Ser
        115                 120

<210> SEQ ID NO 101
<211> LENGTH: 30
<212> TYPE: DNA
<213> ORGANISM: Artificial Sequence
<220> FEATURE:
<223> OTHER INFORMATION: Synthetic

<400> SEQUENCE: 101
ggtggctcca tcagcagtgg tggttactac                                       30

<210> SEQ ID NO 102
<211> LENGTH: 10
<212> TYPE: PRT
<213> ORGANISM: Artificial Sequence
<220> FEATURE:
<223> OTHER INFORMATION: Synthetic

<400> SEQUENCE: 102

Gly Gly Ser Ile Ser Ser Gly Gly Tyr Tyr
1               5                   10

<210> SEQ ID NO 103
<211> LENGTH: 21
<212> TYPE: DNA
<213> ORGANISM: Artificial Sequence
<220> FEATURE:
<223> OTHER INFORMATION: Synthetic

<400> SEQUENCE: 103
atccattata gtgggaacac c                                                21

<210> SEQ ID NO 104
<211> LENGTH: 7
<212> TYPE: PRT
<213> ORGANISM: Artificial Sequence
<220> FEATURE:
<223> OTHER INFORMATION: Synthetic

<400> SEQUENCE: 104

Ile His Tyr Ser Gly Asn Thr
1               5

<210> SEQ ID NO 105
<211> LENGTH: 39

<212> TYPE: DNA
<213> ORGANISM: Artificial Sequence
<220> FEATURE:
<223> OTHER INFORMATION: Synthetic

<400> SEQUENCE: 105
gcgaggaata tggttcgggg agttcactgg ttcgacccc                       39

<210> SEQ ID NO 106
<211> LENGTH: 13
<212> TYPE: PRT
<213> ORGANISM: Artificial Sequence
<220> FEATURE:
<223> OTHER INFORMATION: Synthetic

<400> SEQUENCE: 106

Ala Arg Asn Met Val Arg Gly Val His Trp Phe Asp Pro
1               5                  10

<210> SEQ ID NO 107
<211> LENGTH: 324
<212> TYPE: DNA
<213> ORGANISM: Artificial Sequence
<220> FEATURE:
<223> OTHER INFORMATION: Synthetic

<400> SEQUENCE: 107
gaaatagtgt tgacacagtc tccaggcacc ctgtctttgt ctccagggga gagagccacc    60
ctcttctgtt gggccagtcg gagtgttagc agcagctact tagcctggta ccagcagaaa   120
cctggccagg ctcccaggct cctcatctct ggtgcatcca gcagggccac tggcatccca   180
gacaggttca gtggcagtgg gtctgggaca gacttcactc tcaccatcag cagactggag   240
cctgaagatt ttgcagtata tttctgtcaa cagtatagta gttcaccgct cactttcggc   300
ggagggacca agctggagat caaa                                          324

<210> SEQ ID NO 108
<211> LENGTH: 108
<212> TYPE: PRT
<213> ORGANISM: Artificial Sequence
<220> FEATURE:
<223> OTHER INFORMATION: Synthetic

<400> SEQUENCE: 108

Glu Ile Val Leu Thr Gln Ser Pro Gly Thr Leu Ser Leu Ser Pro Gly
1               5                  10                  15

Glu Arg Ala Thr Leu Phe Cys Trp Ala Ser Arg Ser Val Ser Ser Ser
            20                  25                  30

Tyr Leu Ala Trp Tyr Gln Gln Lys Pro Gly Gln Ala Pro Arg Leu Leu
        35                  40                  45

Ile Ser Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Phe Cys Gln Gln Tyr Ser Ser Ser Pro
                85                  90                  95

Leu Thr Phe Gly Gly Gly Thr Lys Leu Glu Ile Lys
            100                 105

<210> SEQ ID NO 109
<211> LENGTH: 21
<212> TYPE: DNA
<213> ORGANISM: Artificial Sequence

```
<220> FEATURE:
<223> OTHER INFORMATION: Synthetic

<400> SEQUENCE: 109
cggagtgtta gcagcagcta c                                              21

<210> SEQ ID NO 110
<211> LENGTH: 7
<212> TYPE: PRT
<213> ORGANISM: Artificial Sequence
<220> FEATURE:
<223> OTHER INFORMATION: Synthetic

<400> SEQUENCE: 110

Arg Ser Val Ser Ser Ser Tyr
 1               5

<210> SEQ ID NO 111
<211> LENGTH: 9
<212> TYPE: DNA
<213> ORGANISM: Artificial Sequence
<220> FEATURE:
<223> OTHER INFORMATION: Synthetic

<400> SEQUENCE: 111 ggtgcatcc                                                             9

<210> SEQ ID NO 112
<211> LENGTH: 3
<212> TYPE: PRT
<213> ORGANISM: Artificial Sequence
<220> FEATURE:
<223> OTHER INFORMATION: Synthetic

<400> SEQUENCE: 112

Gly Ala Ser
 1

<210> SEQ ID NO 113
<211> LENGTH: 27
<212> TYPE: DNA
<213> ORGANISM: Artificial Sequence
<220> FEATURE:
<223> OTHER INFORMATION: Synthetic

<400> SEQUENCE: 113
caacagtata gtagttcacc gctcact                                        27

<210> SEQ ID NO 114
<211> LENGTH: 9
<212> TYPE: PRT
<213> ORGANISM: Artificial Sequence
<220> FEATURE:
<223> OTHER INFORMATION: Synthetic

<400> SEQUENCE: 114

Gln Gln Tyr Ser Ser Ser Pro Leu Thr
 1               5

<210> SEQ ID NO 115
<211> LENGTH: 369
<212> TYPE: DNA
<213> ORGANISM: Artificial Sequence
<220> FEATURE:
<223> OTHER INFORMATION: Synthetic

<400> SEQUENCE: 115
```

```
caggtgcagc tggtggagtc tgggggaggc gtggtccagc ctgggaggtc cctgagactc      60
tcctgtgcag cgtctggatt caccttcagt agttatggca tgcactgggt ccgccaggct     120
ccaggcaagg ggctggagtg ggtgtcattt ttatggtatg atggaactaa taaaaactat     180
gtagagtccg tgaagggccg attcaccatc tcaagagaca attccaagaa tatgctgtat     240
ctggaaatga acagcctgag agccgaggac acggctgtgt attactgtgc gagagatcac     300
gattttagga gtggttatga ggggtggttc gaccccctggg gccagggaac cctggtcacc     360
gtctcctca                                                             369
```

<210> SEQ ID NO 116
<211> LENGTH: 123
<212> TYPE: PRT
<213> ORGANISM: Artificial Sequence
<220> FEATURE:
<223> OTHER INFORMATION: Synthetic

<400> SEQUENCE: 116

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Phe Leu Trp Tyr Asp Gly Thr Asn Lys Asn Tyr Val Glu Ser Val
    50                  55                  60

Lys Gly Arg Phe Thr Ile Ser Arg Asp Asn Ser Lys Asn Met Leu Tyr
65                  70                  75                  80

Leu Glu Met Asn Ser Leu Arg Ala Glu Asp Thr Ala Val Tyr Tyr Cys
                85                  90                  95

Ala Arg Asp His Asp Phe Arg Ser Gly Tyr Glu Gly Trp Phe Asp Pro
            100                 105                 110

Trp Gly Gln Gly Thr Leu Val Thr Val Ser Ser
        115                 120

<210> SEQ ID NO 117
<211> LENGTH: 321
<212> TYPE: DNA
<213> ORGANISM: Artificial Sequence
<220> FEATURE:
<223> OTHER INFORMATION: Synthetic

<400> SEQUENCE: 117

```
gaaatagtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcaacac cgtagcaact ggcctccac tttcggcgga     300 gggaccaagg tggaaatcaa a                                               321
```

<210> SEQ ID NO 118
<211> LENGTH: 107
<212> TYPE: PRT
<213> ORGANISM: Artificial Sequence
<220> FEATURE:
<223> OTHER INFORMATION: Synthetic

<400> SEQUENCE: 118

-continued

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65              70                  75                      80

Glu Asp Phe Ala Val Tyr Tyr Cys Gln His Arg Ser Asn Trp Pro Pro
             85                  90                  95

Thr Phe Gly Gly Gly Thr Lys Val Glu Ile Lys
             100                 105
```